(12) United States Patent
Mueller et al.

(10) Patent No.: US 7,842,052 B2
(45) Date of Patent: *Nov. 30, 2010

(54) NECKLIFT PROCEDURE AND INSTRUMENTS FOR PERFORMING SAME

(75) Inventors: Gregory Paul Mueller, Beverly Hills, CA (US); Corbett W. Stone, San Diego, CA (US)

(73) Assignee: Implicitcare, LLC, Beverly Hills, CA (US)

( * ) Notice: Subject to any disclaimer, the term of this patent is extended or adjusted under 35 U.S.C. 154(b) by 176 days.

This patent is subject to a terminal disclaimer.

(21) Appl. No.: 11/950,378

(22) Filed: Dec. 4, 2007

(65) Prior Publication Data

US 2008/0132921 A1 Jun. 5, 2008

Related U.S. Application Data

(63) Continuation-in-part of application No. 11/566,386, filed on Dec. 4, 2006, now Pat. No. 7,740,647.

(51) Int. Cl.
*A61B 17/04* (2006.01)
(52) U.S. Cl. .................. 606/148; 606/215; 606/216
(58) Field of Classification Search .......... 606/18, 606/148, 232, 215–217, 233, 228; 602/572, 602/42–47; 600/37; 220/235; 206/570–572, 206/363–367; 623/15.12; 128/898
See application file for complete search history.

(56) References Cited

U.S. PATENT DOCUMENTS

| | | | |
|---|---|---|---|
| 1,353,587 A | 9/1920 | Heck | |
| 1,358,753 A | 11/1920 | Killam et al. | |
| 3,549,049 A | 12/1970 | Weber | |
| 3,983,878 A | 10/1976 | Kawchitch | |

(Continued)

OTHER PUBLICATIONS

Declaration under 37 CFR 1.56 of Gregory Mueller describing a procedure that was used more than one year prior to the filing date of the referenced application. The Examiner is invited to contact applicant's attorney should he/she have any questions regarding the declaration.

(Continued)

*Primary Examiner*—Gary Jackson
*Assistant Examiner*—Son Dang
(74) *Attorney, Agent, or Firm*—Jeffer Mangels Butler & Mitchell LLP

(57) ABSTRACT

A method for threading a suture in a patient's body. The method includes the steps of providing a suture, providing a threading device comprising an elongated rod having a suture tie-off location and first and second ends, tying the suture to the suture tie-off location, inserting the first end of the elongated rod through a first opening in the patient's skin, passing the first end of the elongated rod subcutaneously to a second opening in the patient's skin, pulling the first end of the elongated rod and a portion of the suture through the second opening, without turning the elongated rod around, and passing the second end of the elongated rod subcutaneously to an opening in the patient's skin. At least one point during the performance of the method the first end of the elongated rod extends out of the first opening and the second end of the elongated rod extends through the second opening. In a preferred embodiment, the first and second ends of the threading device are each lighted at predetermined points during the method.

16 Claims, 33 Drawing Sheets

U.S. PATENT DOCUMENTS

| | | | |
|---|---|---|---|
| 4,302,797 A | 11/1981 | Cooper | |
| 4,351,333 A * | 9/1982 | Lazarus et al. | 604/28 |
| 4,886,079 A * | 12/1989 | Mooney | 132/319 |
| 5,077,901 A | 1/1992 | Warner et al. | |
| 5,222,508 A | 6/1993 | Contarini | |
| 5,337,735 A | 8/1994 | Salerno | |
| 5,391,156 A | 2/1995 | Hildwein | |
| 5,391,175 A | 2/1995 | Sharpe | |
| 5,437,726 A | 8/1995 | Proto | |
| 5,697,950 A | 12/1997 | Fucci | |
| 5,728,103 A | 3/1998 | Picha | |
| 5,769,791 A | 6/1998 | Benaron | |
| 5,797,929 A | 8/1998 | Andreas | |
| 5,879,306 A | 3/1999 | Fontenot | |
| 5,921,673 A | 7/1999 | Habel | |
| 5,941,855 A | 8/1999 | Picha | |
| 5,951,543 A | 9/1999 | Brauer | |
| 6,029,323 A | 2/2000 | Dickie et al. | |
| 6,062,785 A | 5/2000 | McDermott | |
| 6,152,951 A | 11/2000 | Hashimoto | |
| 6,162,211 A | 12/2000 | Tankovich | |
| 6,245,091 B1 | 6/2001 | Buncke | |
| 6,391,023 B1 | 5/2002 | Weber et al. | |
| 6,432,101 B1 | 8/2002 | Weber et al. | |
| 6,432,970 B2 | 8/2002 | Beachy et al. | |
| 6,436,035 B1 | 8/2002 | Toth | |
| 6,478,442 B2 | 11/2002 | Chen | |
| 6,500,184 B1 | 12/2002 | Chan | |
| 6,663,618 B2 | 12/2003 | Weber | |
| 6,945,777 B2 | 9/2005 | Black | |
| 6,974,450 B2 | 12/2005 | Weber | |
| 7,048,682 B2 | 5/2006 | Neisz | |
| 7,060,079 B2 | 6/2006 | Wulc | |
| 7,270,439 B2 | 9/2007 | Horrell | |
| 7,494,488 B2 | 2/2009 | Weber | |
| 2001/0001260 A1 | 5/2001 | Parker | |
| 2001/0025190 A1 | 9/2001 | Weber et al. | |
| 2002/0019670 A1 | 2/2002 | Crawley et al. | |
| 2002/0029011 A1 | 3/2002 | Dyer | |
| 2002/0064302 A1 | 5/2002 | Massengill | |
| 2002/0198544 A1 | 12/2002 | Uflacker | |
| 2003/0014041 A1 | 1/2003 | Weber et al. | |
| 2004/0002735 A1 | 1/2004 | Lizardi | |
| 2004/0105278 A1 | 6/2004 | Currie et al. | |
| 2004/0122451 A1 | 6/2004 | Wood | |
| 2004/0133216 A1 | 7/2004 | Wulc | |
| 2004/0167574 A1 | 8/2004 | Kuyava et al. | |
| 2004/0267314 A1 | 12/2004 | Wolf et al. | |
| 2004/0267315 A1 | 12/2004 | Wolf | |
| 2005/0055073 A1 | 3/2005 | Weber | |
| 2005/0099824 A1 | 5/2005 | Dowling | |
| 2005/0203576 A1 | 9/2005 | Sulamanidze | |
| 2005/0240224 A1 * | 10/2005 | Wu | 606/228 |
| 2005/0248933 A1 | 11/2005 | Chen | |
| 2005/0256535 A1 | 11/2005 | Capurro | |
| 2005/0267531 A1 | 12/2005 | Ruff et al. | |
| 2005/0267532 A1 | 12/2005 | Wu | |
| 2006/0079935 A1 | 4/2006 | Kolster | |
| 2006/0095103 A1 | 5/2006 | Eggers | |
| 2006/0217596 A1 | 9/2006 | Williams | |
| 2006/0293555 A1 | 12/2006 | Salter | |
| 2008/0312685 A1 * | 12/2008 | O'Malley et al. | 606/216 |
| 2009/0082791 A1 | 3/2009 | Schroeder et al. | |

OTHER PUBLICATIONS

Ishizaka, Kazuhiro et al., "A Light-Guide Needle for Subureteric Injection of Materials to Treat Vesicoureteral Reflux (VUR)", Department of Urology, Tokio Medical and Dental University School of Medicine, Tokyo, Japan, Engineering & Urology Society, 14th Annual Meeting (May 1999).

International Search Report and Written Opinion of the International Searching Authority, issued Jan. 11, 2010, in related PCT Application No. PCT/US2009/057089.

* cited by examiner

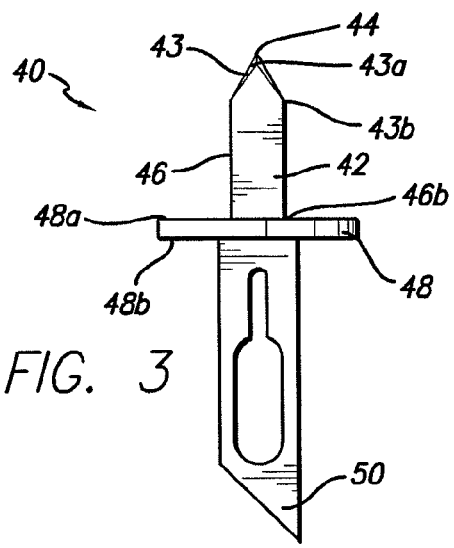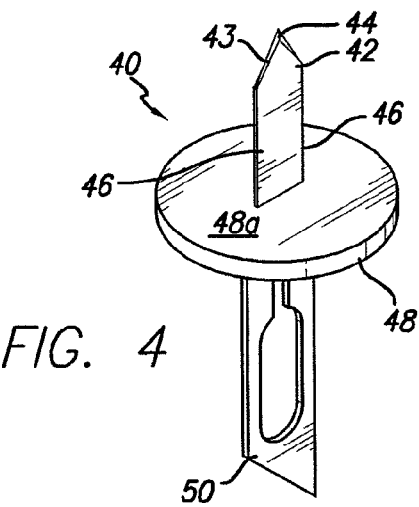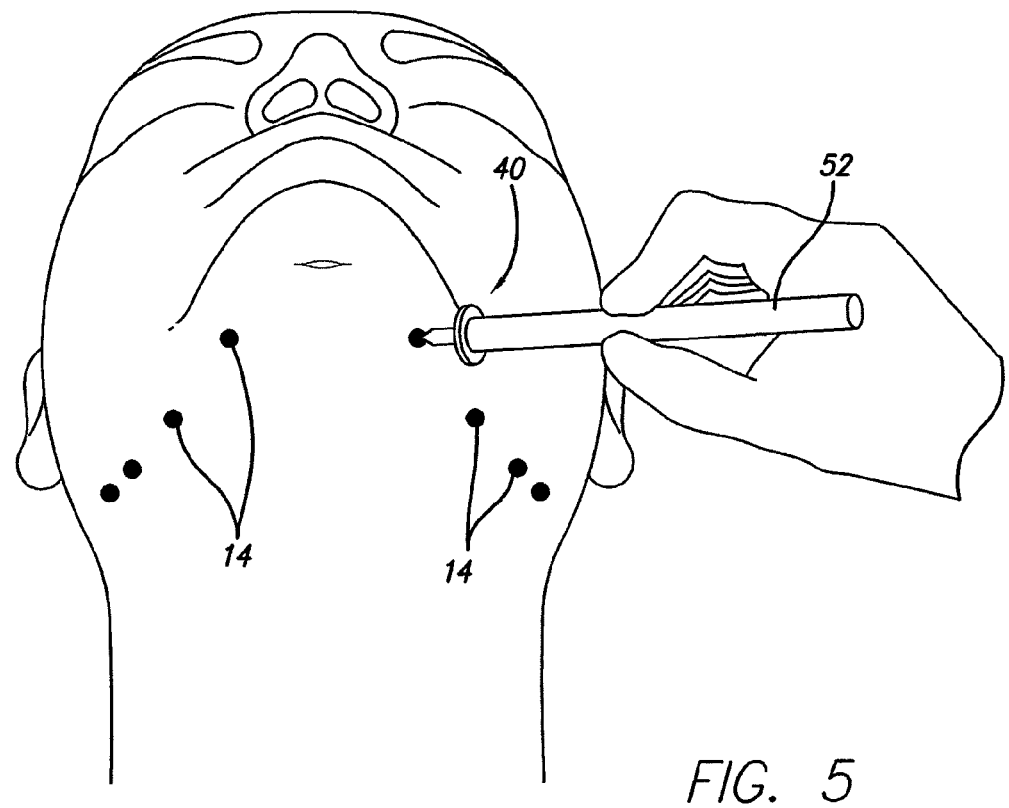

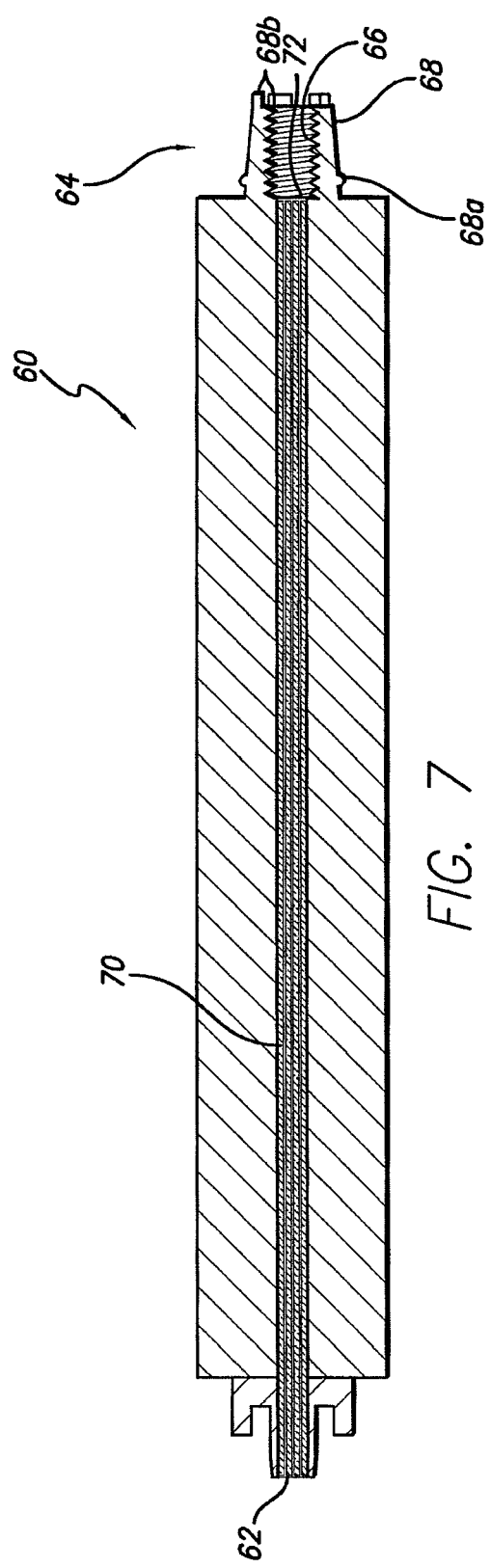
FIG. 6
FIG. 7

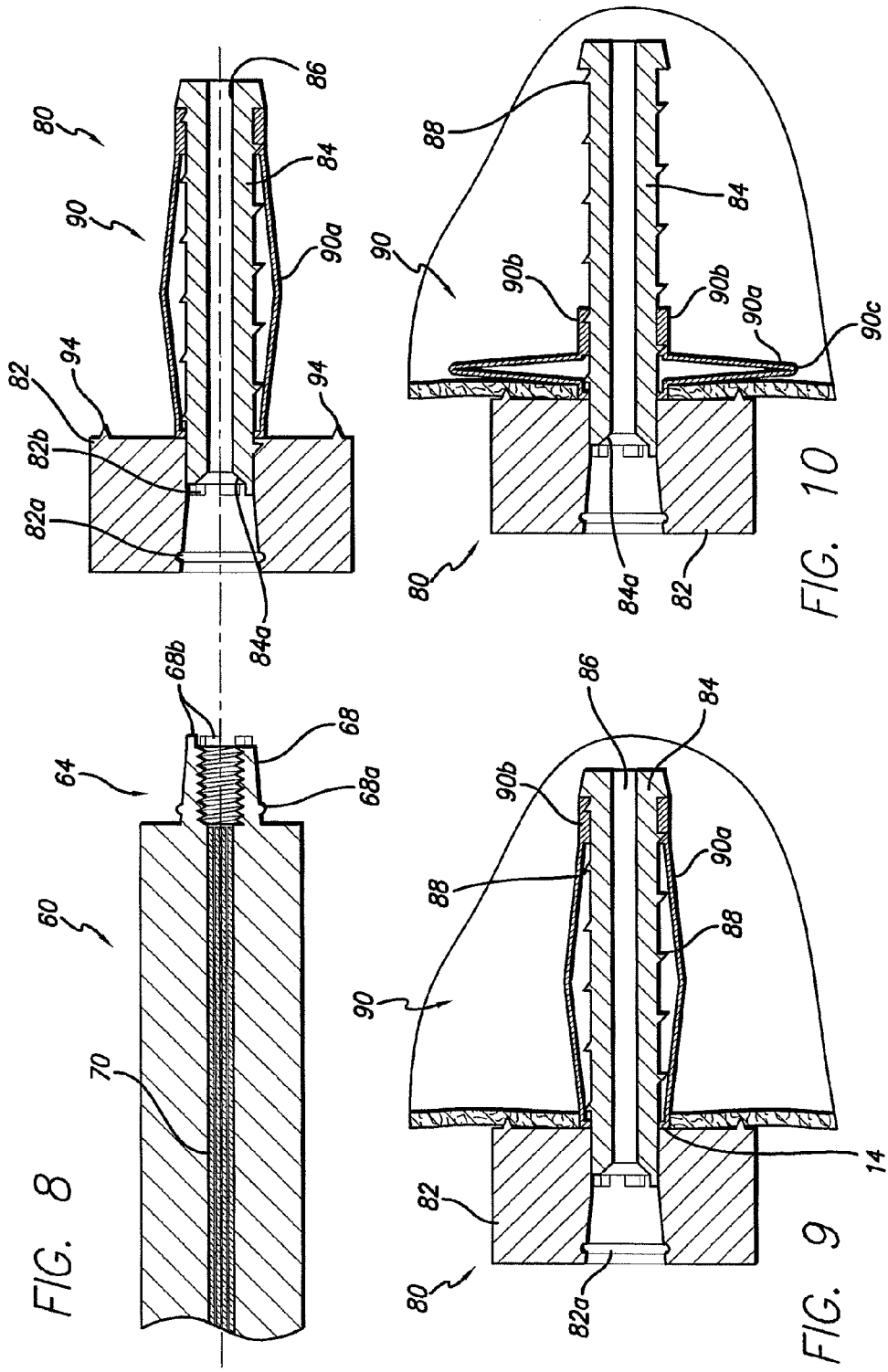

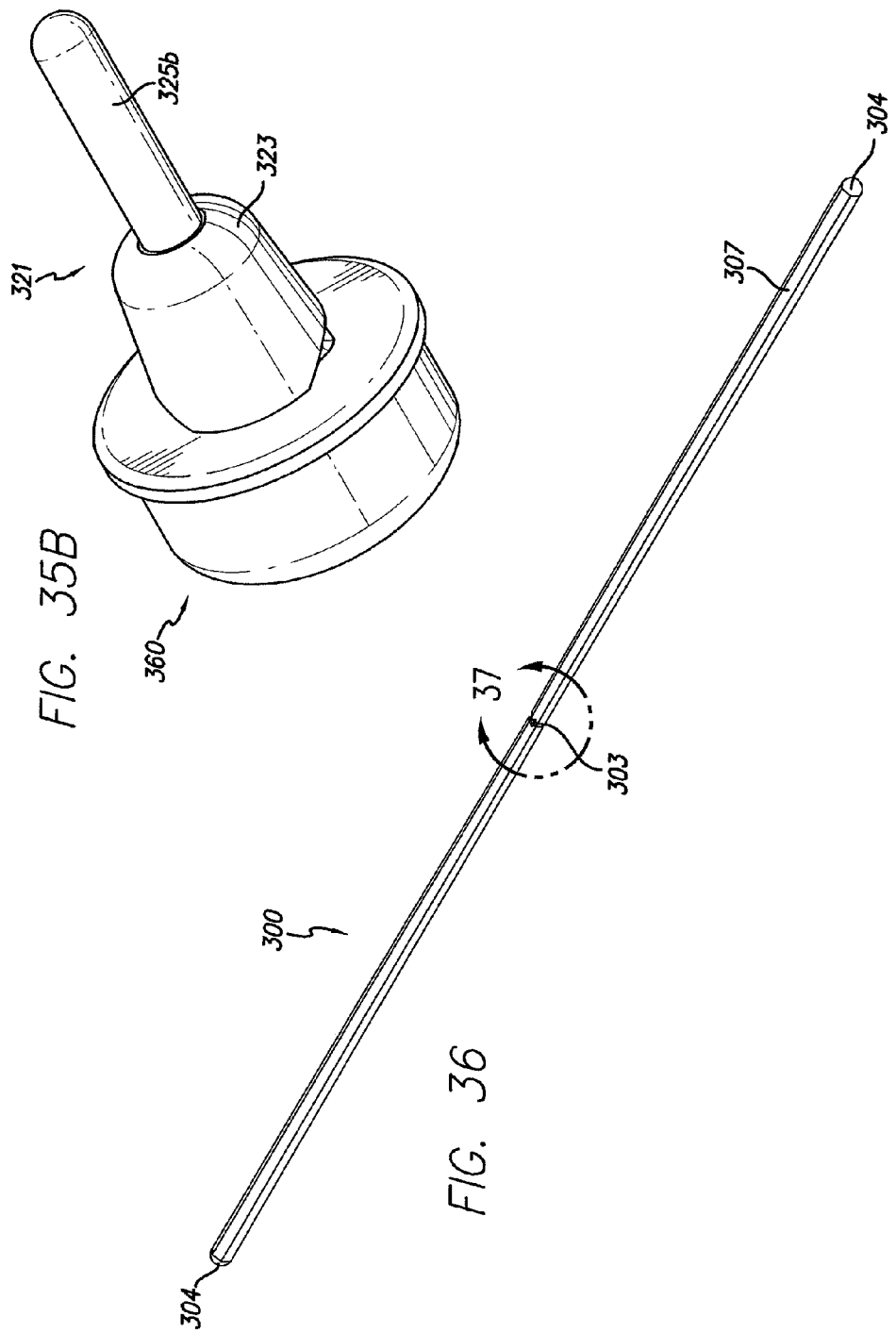

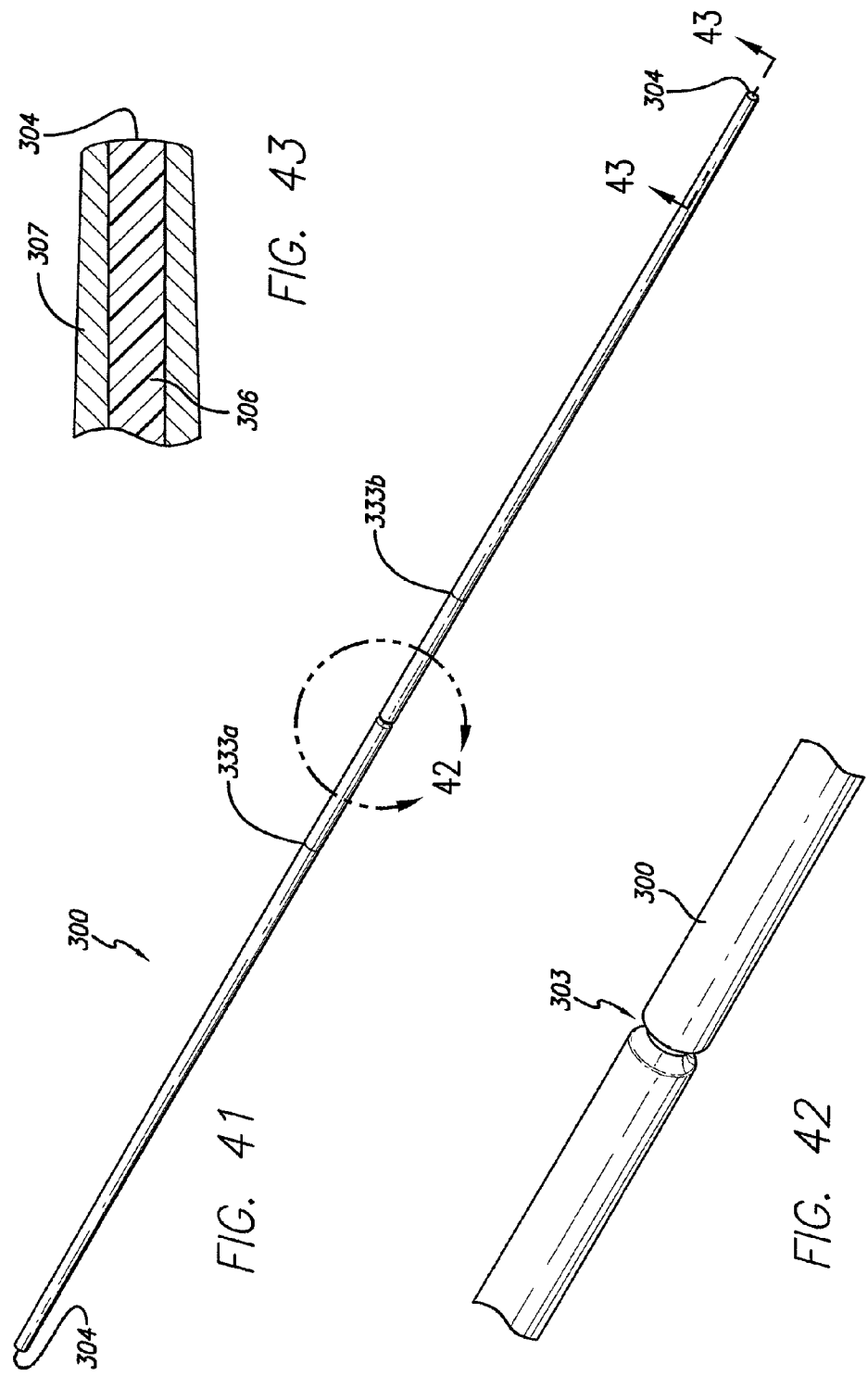

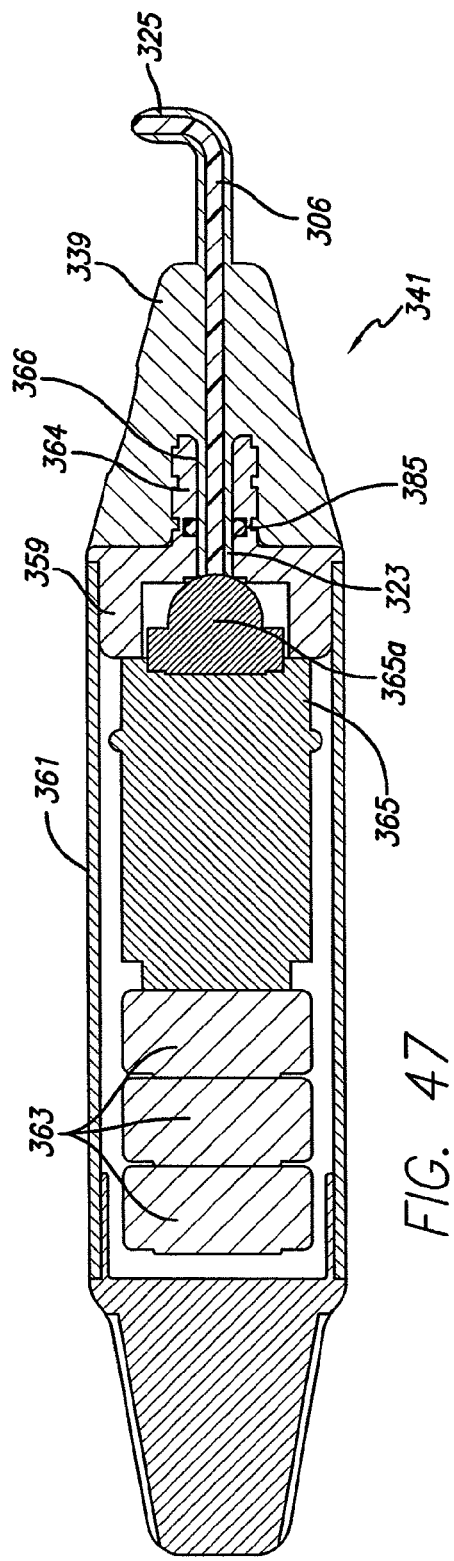
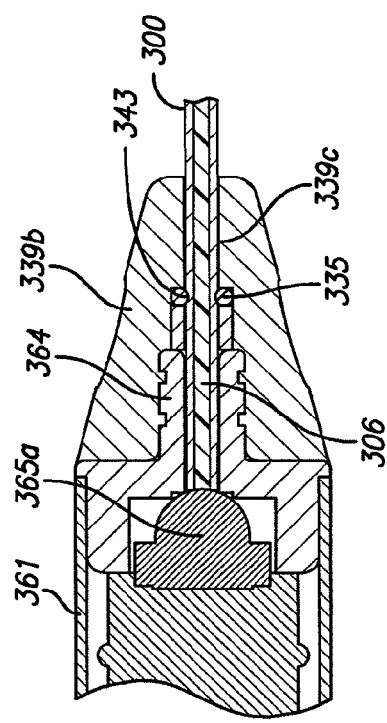
FIG. 47
FIG. 48

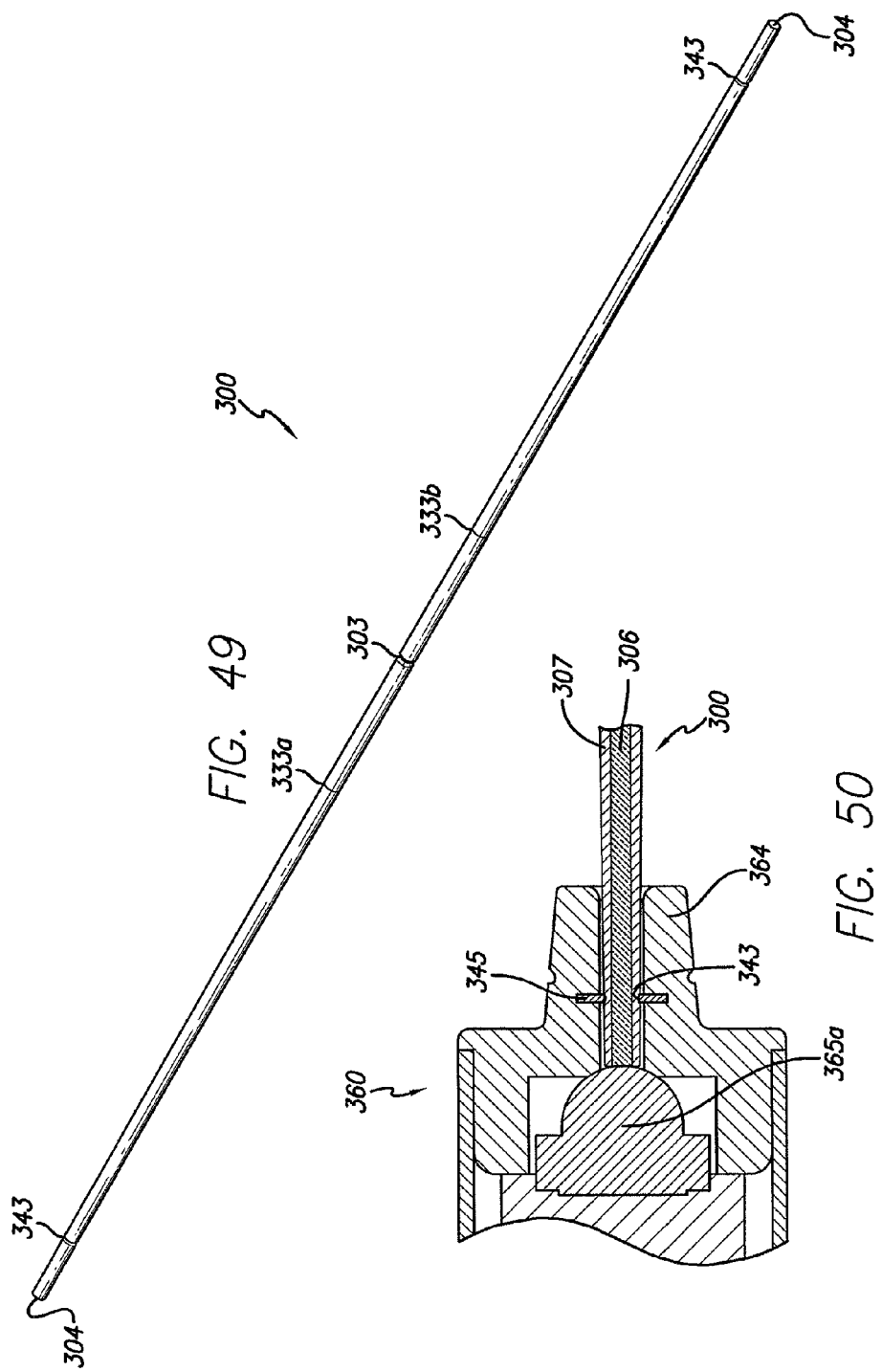

NECKLIFT PROCEDURE AND INSTRUMENTS FOR PERFORMING SAME

This application is a continuation-in-part of U.S. patent application Ser. No. 11/566,386, filed Dec. 4, 2006, the entirety of which is incorporated herein by reference.

FIELD OF THE INVENTION

The present invention relates generally to methods and devices for plastic surgery and, more particularly, to a necklift procedure that is minimally invasive and to instruments for performing the procedure.

BACKGROUND OF THE INVENTION

Conventional neck rejuvenation surgeons advocate procedures that alter the anatomy of the neck to restore a more youthful neck contour. These involve platysmal manipulation such as muscle advancement and/or division, and frequently sub-platysmal fat excision. Partial resection of submandibular gland tissue may be performed as well. These techniques vary in complexity and may result in significant complications, including post-operative bleeding, nerve injury, permanent visible skin deformities caused by muscle division, or over-resection of fat.

Plastic and reconstructive surgeons have long sought to develop methods and devices to aid in the support of physical structures that have lost their natural tension and support. The most often treated areas include the face, the chest region, the buttocks and other regions that lose tension and sag. Current devices are not always adequate in providing a natural-looking structure to prevent such loss of tension in these structures.

The aging process causes gradual and predictable changes in the soft tissue layers of the lower face and neck, the anatomical basis of which has been well documented. Loss of elasticity and fragmentation of collagen results in rhytid formation and skin redundancy. Subcutaneous fat thickens and droops or is ptotic and becomes more noticeable. Stretching of the fascia and musculature results in a loss of the supporting 'sling' of the submentum, often resulting in submandibular gland ptosis. Further loss of tone and muscular atrophy results in banding of the medial platysmal borders, blunting of the cervicomental angle and loss of lateral mandibular definition.

The classical necklift's failure in adequately addressing the consequences of aging in the neck has prompted the development of a number of modifications and adjunctive procedures. These include skin excisions, various lipoplasty techniques, anterior or posteriorly based platysmal transection, resection, or plication procedures, SMAS-platysma flaps, and even suture suspension techniques. However, these modifications have their limitations.

Problems with scar contractures and hypertrophic scarring have resulted in the near abandonment of midline skin excision with subsequent Z, W or T-plasty. Liposuction or direct lipocontouring plays an important role in the aging neck.

SUMMARY OF THE PREFERRED EMBODIMENTS

In accordance with a first aspect of the present invention, there is provided a method for threading a suture in a patient's body. The method includes the steps of providing a suture, providing a threading device comprising an elongated rod having a suture tie-off location and first and second ends, tying the suture to the suture tie-off location, inserting the first end of the elongated rod through a first opening in the patient's skin, passing the first end of the elongated rod subcutaneously to a second opening in the patient's skin, pulling the first end of the elongated rod and a portion of the suture through the second opening, without turning the elongated rod around, and passing the second end of the elongated rod subcutaneously to an opening in the patient's skin. At least one point during the performance of the method the first end of the elongated rod extends out of the first opening and the second end of the elongated rod extends through the second opening. In a preferred embodiment, the first and second ends of the threading device are each lighted at predetermined points during the method.

In accordance with another aspect of the present invention, there is provided a method of performing surgery. The method includes the steps of placing a tape template onto a portion of a patient's skin, marking a plurality of access sites, making an opening to form a mid-line access site, performing liposuction, forming a plurality of openings in the skin at the access sites, providing a threading device having a suture secured thereto, and inserting the threading device and suture through a plurality of access sites to form a suture matrix under the skin.

In accordance with yet another aspect of the present invention, there is provided a surgical kit that includes at least two of the following at least one tape member, a lancet, a handset, a clearing device, a nose cone, a threading device, and a suture. In a preferred embodiment, the handset includes a tubular member having first and second opposite, an instrument dock extending from the first end of the tubular member that includes an opening for receiving a rod, and a light source, wherein light from the light source is directed out of the opening in the instrument dock. The threading device preferably includes an elongated rod having a groove defined therein that extends at least substantially circumferentially around the rod, and blunt ends. The threading device also preferably includes an elongated tube having first and second open ends and a suture tie-off location disposed approximately halfway between the first and second ends, and a light guide running through the elongated tube. The light guide has first and second ends that are substantially flush with the first and second ends of the tube. The tape member preferably includes a first layer that has at least two perforations defined therethrough, and a second layer overlying the first layer that has at least two perforations defined therethrough. At least one of the perforations of the second layer at least partially overlaps at least one of the perforations of the first layer. The clearing device preferably includes a neck and a clearing portion extending from the neck in a curved path that defines a plane that is approximately perpendicular to the longitudinal axis of the neck.

BRIEF DESCRIPTION OF THE DRAWINGS

The invention may be more readily understood by referring to the accompanying drawings in which:

FIG. 3 is a front elevational view of a lancet in accordance with a preferred embodiment of the present invention;

FIG. 4 is a perspective view of the lancet of FIG. 3;

FIG. 5 is a view of the lancet of FIG. 3 being used to make a puncture;

FIG. 6 is a side elevational view of a handset in accordance with a preferred embodiment of the present invention;

FIG. 7 is a sectional side elevational view of the handset of FIG. 5 showing the fiberoptic core;

FIG. 8 is a cross-sectional view of the handset of FIG. 5 before docking with a skin port in accordance with a preferred embodiment of the present invention;

FIG. 9 is a cross-sectional view showing the skin port inserted through a patient's skin before deployment;

FIG. 10 is a cross-sectional view showing the skin port inserted through a patient's skin after deployment;

FIG. 35b is a perspective view of another clearing device secured on the end of the handset of FIG. 28;

FIG. 36 is a perspective view of a threading device in accordance with a preferred embodiment of the present invention;

FIG. 41 is a perspective view of a threading rod in accordance with a preferred embodiment of the present invention;

FIG. 42 is a detailed perspective view of the threading rod of FIG. 41 showing the groove;

FIG. 43 is a cross-sectional elevation of an end of the threading rod of FIG. 41 taken along line 43-43 of FIG. 41;

FIG. 47 is a cross-sectional elevational view of a handset with a clearing device assembly thereon in accordance with another preferred embodiment of the present invention;

FIG. 48 is a partial cross-sectional elevational view of a handset with a nose cone thereon in accordance with another preferred embodiment of the present invention;

FIG. 49 is a perspective view of a threading rod in accordance with another preferred embodiment of the present invention;

FIG. 50 is a partial cross-sectional elevational view of a handset with the threading rod of FIG. 49 secured therein;

Like numerals refer to like parts throughout the several views of the drawings.

DETAILED DESCRIPTION OF THE PREFERRED EMBODIMENTS

Described herein are preferred embodiments of a technique for placing a suture in a person's body. The technique is preferably used in the field of plastic surgery and involves several steps which each require specific instrumentation.

For exemplary purposes only, described hereinbelow are preferred embodiments wherein the technique and instruments of the present invention are used to perform a neck lift, referred to herein as Percutaneous Trampoline Platysmaplasty. However, it will be understood that this is not a limitation on the present invention and that the technique and instruments can be used as desired by one of ordinary skill in the art.

The liposuction portion of the procedure is performed without a large incision under the chin. The placement of the suture support matrix is performed through several small access sites in the neck area under the jaw. The advantage is that the entire support system can be placed without the typical large incision under the chin that is necessary for the surgeon to see the operative field. In addition the surgery is less invasive and does not require an extensive dissection of the skin in the area under the chin.

Figure 25:
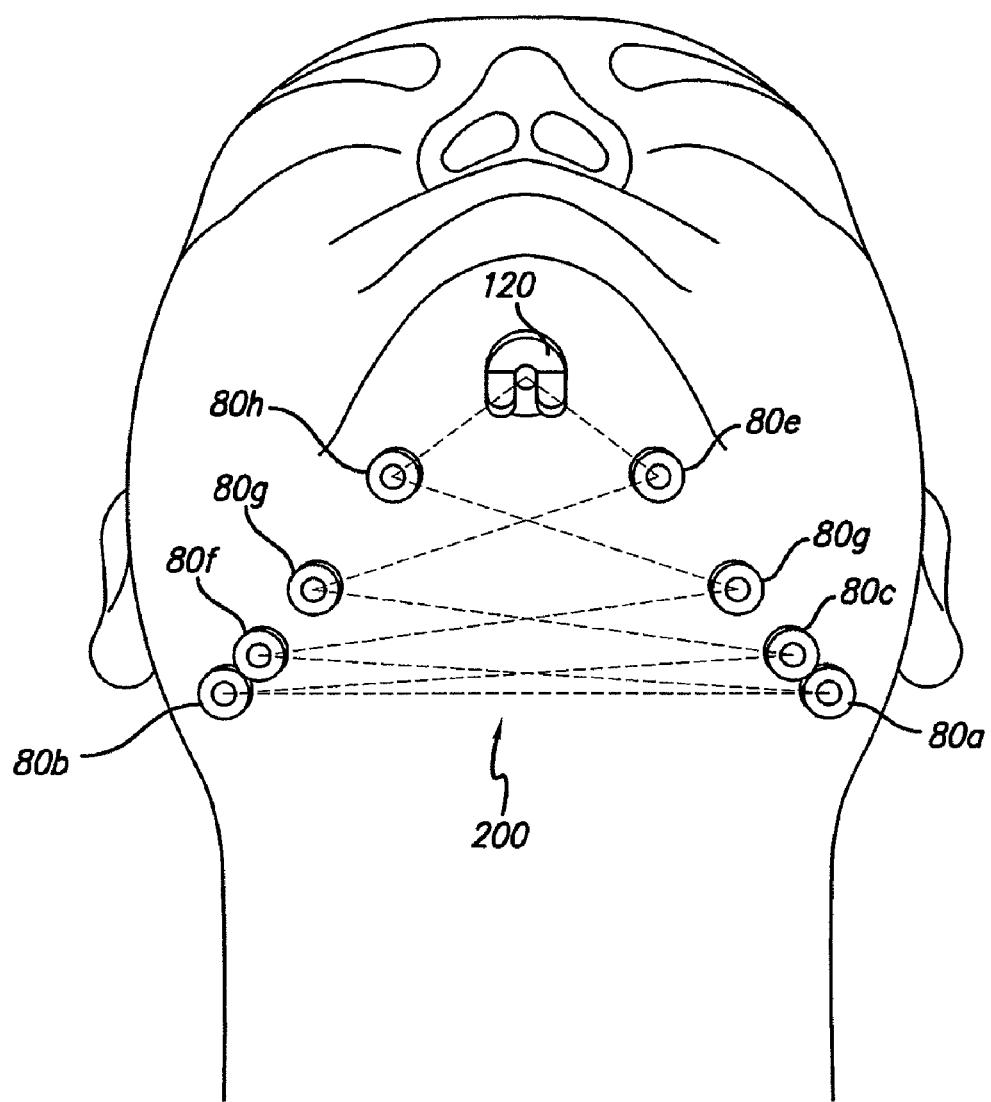
FIG. 25 is a view of a patient with the support matrix shown in hidden lines.
Figure 56:
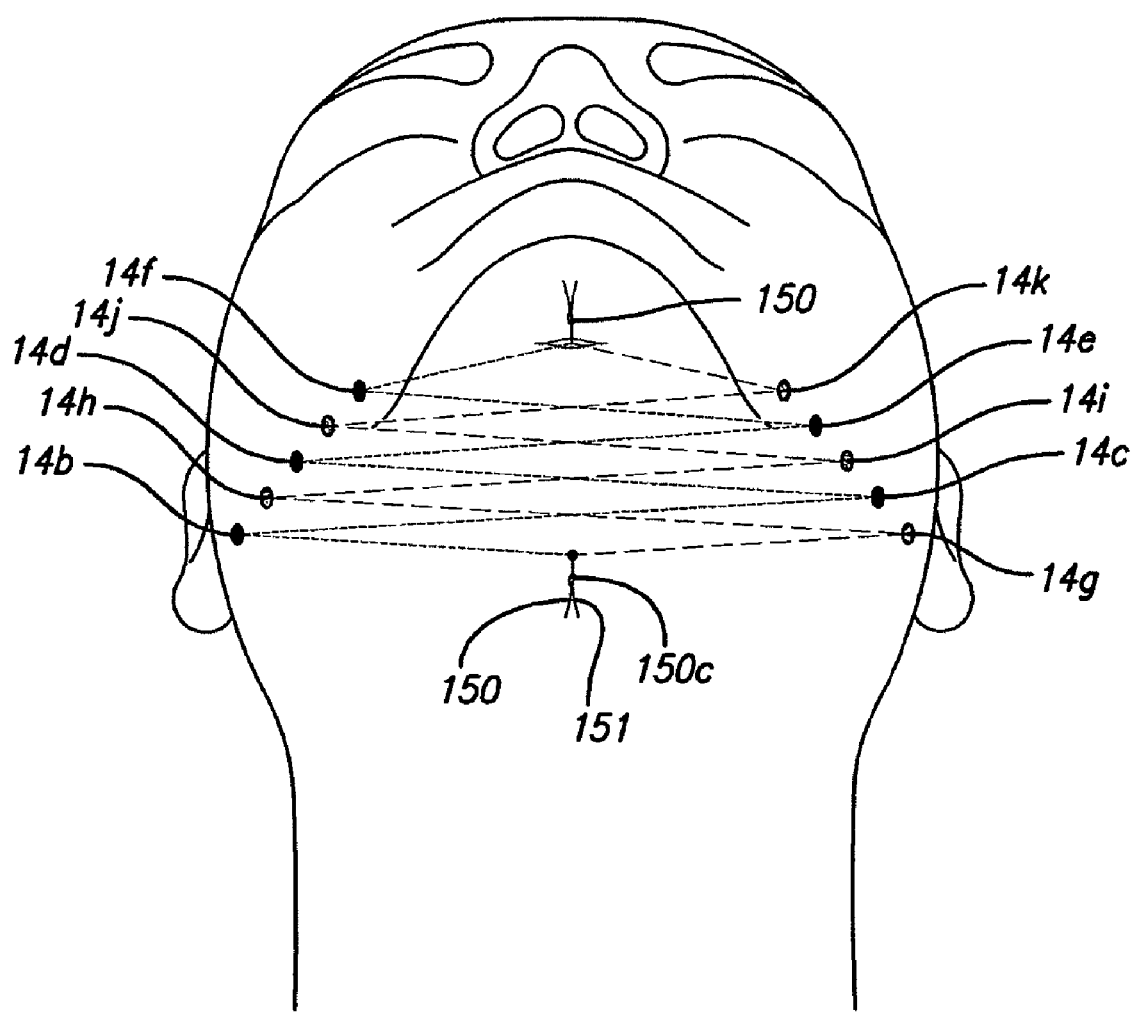
FIG. 56 is a view of a patient showing the final placement of the support matrix with two sutures before the knots have been pushed through the access sites.

The accurate placement of the support suture(s) (also referred to herein as the support structure or support matrix 200 and is shown in FIGS. 25 and 56) will be described herein along with the description of each of the individual instruments or devices that may be used in connection with such procedure.

As described above, the inventive aspects of the present invention involve the placement of the support matrix 200 and not the actual liposuction technique. Therefore, it will be understood that any references to liposuction techniques herein are only exemplary.

It will be appreciated that terms such as "front," "back," "top," "bottom," "side," "right," "left," "upwardly" and "downwardly" used herein are merely for ease of description and refer to the orientation of the components as shown in the figures. It should be understood that any orientation of the instruments and articles and the components thereof described herein is within the scope of the present invention.

Figure 1:
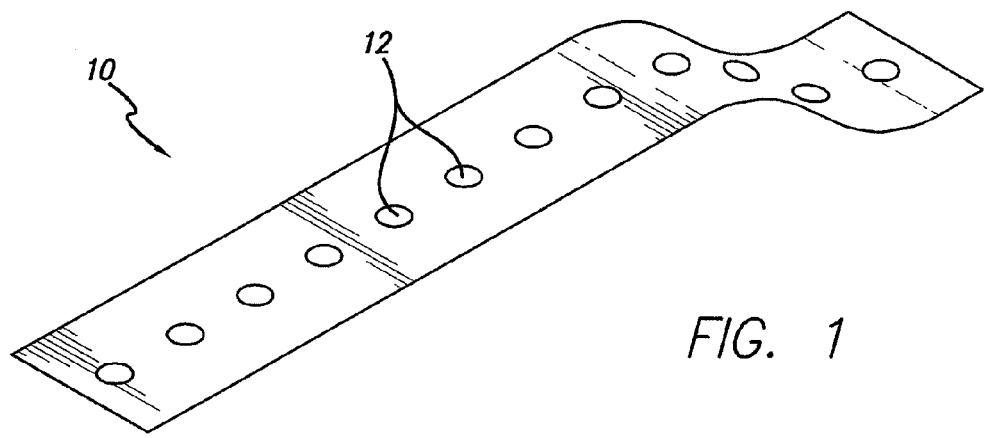
FIG. 1 is a perspective view of a tape template in accordance with a preferred embodiment of the present invention.
Figure 2:
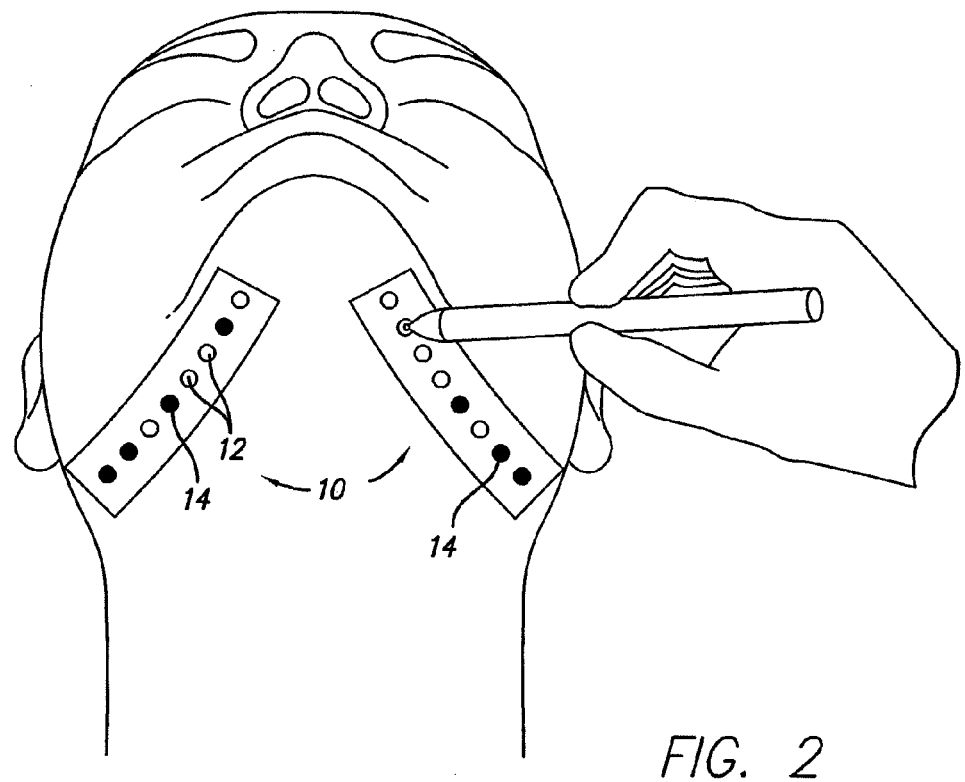
FIG. 2 is a view of the tape template of FIG. 1 being used to mark puncture locations on a patient's chin.

Referring to FIGS. 1-2, template tape (or tape members) 10 will be described. In a preferred embodiment, tape 10 is a clear piece of tape with perforations 12 therethrough that are spaced apart at predetermined locations. Tape 10 includes adhesive thereon so that it can be secured to the patient's skin. In an exemplary embodiment, tape 10 is a one inch wide clear tape with about 2 mm circular perforations 12 defined therethrough that are spaced about every 5 mm along the center of the tape. The perforations 12 are preferably positioned along the longitudinal center of the tape 10, however this is not a limitation on the present invention. In another embodiment, tape 10 is not clear. In a preferred embodiment, tape 10 is provided in roll form. However, this is not a limitation on the present invention.

Tape 10 is used in immediate pre-operative planning to determine the placement of access sites 14, which will determine the placement of the support matrix 200. Tape 10 is used as a guide to help provide proper placement of each suture and its corresponding pivot point (as described below). Perforations 12 are used to mark access sites 14 for the surgery.

In a preferred embodiment, first and second tape members 10 are placed on each side of the skin overlying the undersurface of the mandible, as is shown in FIG. 2. Preferably, tape 10 is utilized with the patient sitting upright, which allows the natural neck contours to be visible. This is not a limitation on the present invention, however. The surgeon uses tape 10 and the plurality of perforations 12 to develop a surgical approach that is individually tailored for each patient, depending on the correction desired. As those skilled in the art will appreciate, placement of the support matrix 200 will be different for different patients depending on the patient's anatomy.

The exemplary 5 mm span between perforations 12 allows placement of pivot points in close proximity. This results in a dense support matrix allowing elevation of muscle and glandular tissue. For example, pivot points may be placed 1-2 cm apart if minimal support is needed. Those skilled in the art will be able to make determinations as to where the access sites 14 should be located based on the patient's needs. For example, as is shown in FIG. 2, the surgeon has only chosen four access sites 14 on each side.

As shown in FIG. 2, after the tape 10 has been placed and the surgeon has determined the structure of the support matrix 200, the surgeon marks skin exposed through the desired perforations 12 with a surgical marking pen or the like. These markings 14 indicate the areas that require suture placement to elevate the soft tissue of the neck. In a preferred embodiment, as is shown in FIGS. 2 and 5, the markings 14 made using the first tape member 10 are symmetrical to the markings 14 made using the second tape member 10.

As will be described below, each of the markings 14 define a location or access site that will be punctured to allow subcutaneous access at that location. For simplicity, because each access site is marked and then punctured, the access sites, markings and punctures will all be labeled 14 herein.

As will be appreciated by those skilled in the art, in areas where significant platysmal banding or glandular ptosis is evident significant support will be required. To achieve this, multiple suture strands will be required. As each area to be elevated is recognized, a corresponding tape perforation 12 is marked 14 to insure that suture placement is accurate.

Figure 26:
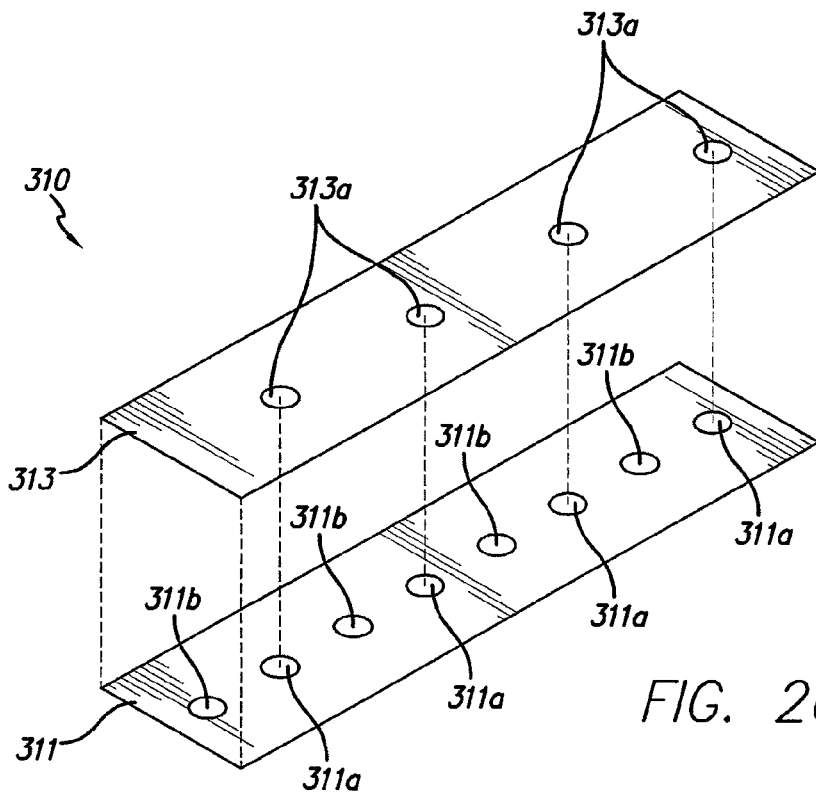
FIG. 26 is an exploded perspective view of a laminated tape template in accordance with a preferred embodiment of the present invention.
Figure 27:
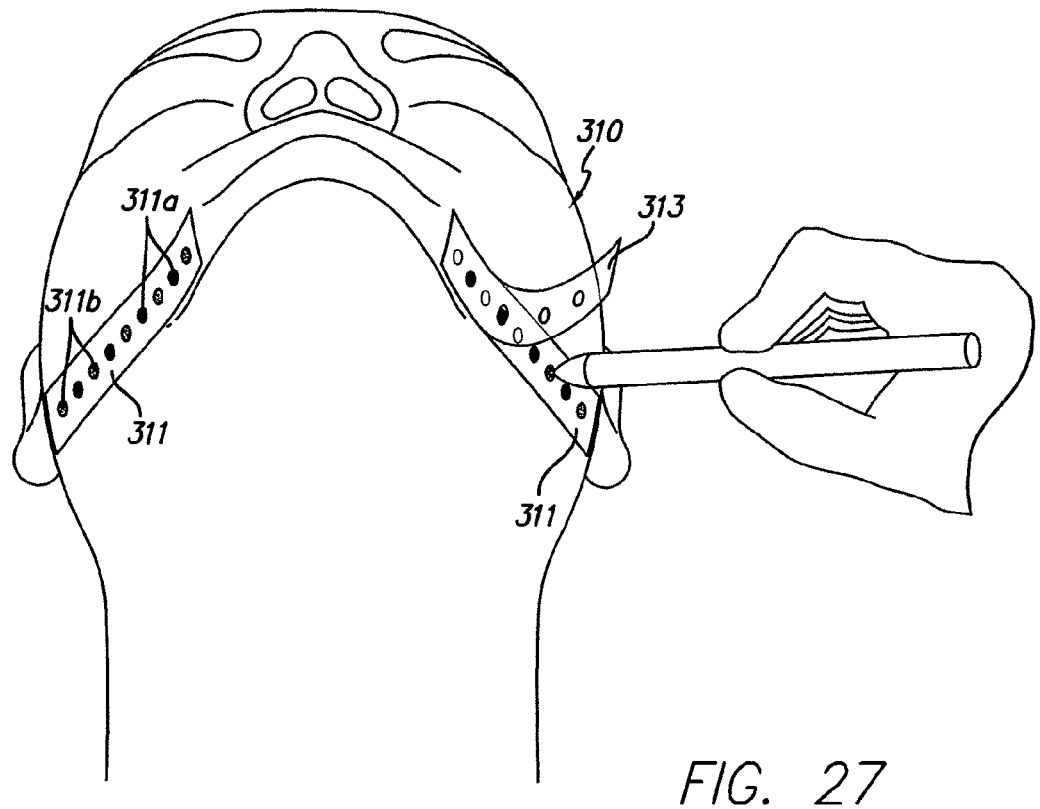
FIG. 27 is a view of the laminated tape template of FIG. 26 being used to mark puncture locations on a patient's chin.
Figure 28:
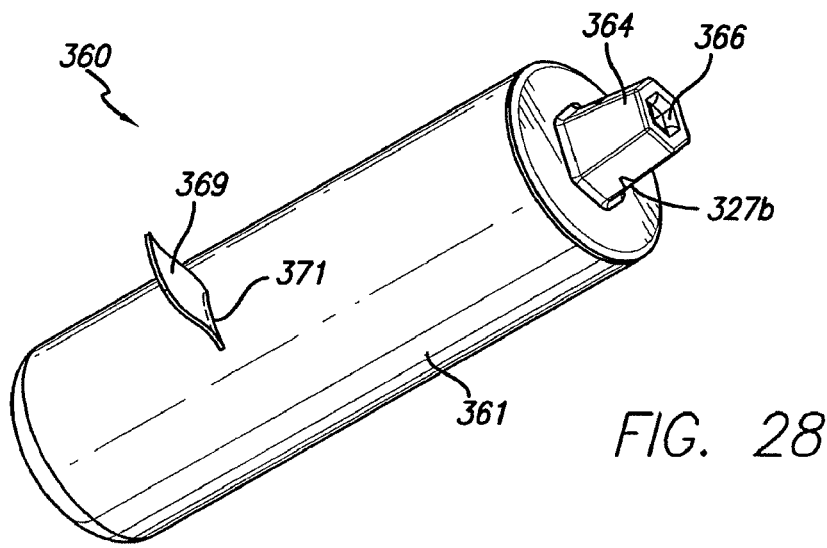
FIG. 28 is a perspective view of a handset in accordance with a preferred embodiment of the present invention.

As shown in FIGS. 26-27, in another preferred embodiment, the tape 310 can be laminated. The laminated tape 310 preferably includes two layers 311 and 313. As shown in FIG. 26, the top layer 313 has one set of holes or perforations 313a and the bottom layer 311 has two sets of perforations 311a and 311b. Perforations 311a and 313a in the different layers 311 and 313 are preferably concentric. However, any amount of overlap between perforations 311a and 313a is within the scope of the present invention. This arrangement of perforations helps the surgeon when marking the patient.

As will described below, the support matrix 200 is formed similar to the way a shoelace is weaved through a shoe. Therefore, in marking the skin for the access sites 14, it can be helpful to mark the skin with two different color markers, for example, red and blue (shown as solid and stippled in the figures). Then, when the matrix 200 is created or the "shoe is laced" the surgeon goes from blue marking to blue marking and red marking to red marking (which each have an access site 14 formed therein, as described below).

In use, the surgeon positions the laminated tape 310 as desired and marks the perforations (the concentric or double perforations 311a and 313a) with the first color. Then, the surgeon peels the first or top layer 313 off, thereby exposing the second set of perforations 311b. The surgeon then marks the second set of perforations 311b with a different color marker. Tape 310 can also be configured in a rolled form. In another preferred embodiment, a single piece of tape 310 can be used that extends all the way around the jaw line or other location on the body. This helps align the markings on each side.

It will be understood that tape 10 or 310 is preferably used before performing liposuction or other desired procedure.

However, this is not a limitation on the present invention. In another embodiment, tape can be used after liposuction is performed. In another embodiment, the tape can be omitted and the surgeon can mark or puncture the skin as desired.

It will appreciated by those skilled in the art that the tape 10 or 310 can be used on areas of the body other than the chin. For example, the tape (and the remainder of the procedure described below) can be used for a face lift or in the MACS-lift or when placing a neck defining suture (both described below).

After the desired markings 14 have been made, the patient is ready for liposuction. It will be understood that when the surgical procedure does not include liposuction, the markings are made before whatever procedure is being performed. The patients head and neck are prepped and draped in a sterile fashion and local anesthetic is injected into the area under the chin. A small opening (referred to herein as the midline submental access site) is made in this area. Tumescent fluid is injected into the entire area under the chin, including the neck region. Liposuction is performed on the entire region. Upon completion, the area is once again infiltrated with the tumescent fluid. This subcutaneous infusion results in the elevation of the skin from the platysma muscle.

With reference to FIGS. 3-5, after completion of liposuction, the patient is ready for placement of the support matrix 200. A lancet 40 is used to create access sites 14 by puncturing the dermis at the points marked using tape 10 or 310.

As shown in FIG. 3, lancet 40 includes a blade 42 that has two sharp edges 43 that end at a point 44 with two blunt edges 46 therebelow. In a preferred embodiment, blade 42 is about 8 mm in length. Blunt edges 46 of blade 42 extend from a flange or stop member 48 that prevents blade 42 from going deeper into the skin than desired. Flange 48 ensures consistent depth of blade penetration. Also, blade 42 is sized to allow placement of skin ports 80 as described below.

Stop member 48 has an upper surface 48*a* and a lower surface 48*b*. The blade 42 extends upwardly from the upper surface 48*a* of the stop member 48. As is shown in FIG. 3, the two sharp edges 43 each have first and second ends 43*a* and 43*b*, respectively and the two blunt edges 46 each have first and second ends 46*a* and 46*b*, respectively.

In a preferred embodiment, the first ends 43*a* of the sharp edges 43 meet at point 44 and extend downwardly from point 44 at an angle of 90° or less. The first ends 46*a* of the two blunt edges 46 extend downwardly from the second ends 43*b* of the two sharp edges 43. The sharp edges 43 and blunt edges 46 meet at an obtuse angle. The second ends 46*b* of the two blunt edges 46 are connected to the stop member 48, which, in a preferred embodiment, is disc-shaped. However, this is not a limitation on the present invention. In an alternative embodiment, the blade 42 can extend from the stop member 48 at a non-right angle (e.g., an acute angle).

In a preferred embodiment, lancet 40 includes an attachment member 50 that extends downwardly from the lower surface 48*b* of the stop member 48 and allows the lancet 40 to be secured on a standard scalpel handle 52. In another embodiment, lancet 40 can be provided with a unitary handle.

The subcutaneous infusion described above results in the elevation of the skin from the platysma muscle. Once infiltrated, the access sites 14 are developed by puncturing of the skin with the percutaneous lancet 40 at the markings developed using tape 10, as shown in FIG. 5. Lancet 40 allows puncturing of the skin in order to gain access to the neck region and preferably ensures that each access site is as small as possible, allowing the placement of the support system 200.

It will be understood that in a preferred embodiment, lancet 40 creates punctures instead of incisions, which minimalizes trauma and the risk of scarring. However, incisions can be used in another embodiment.

Referring to FIGS. 6-7, the next instrument used in the procedure is a handset or handle 60. Handset 60 is embodied in a reusable insertion device with an instrument dock 64 at an end thereof. In a preferred embodiment, handset 60 also includes a fiber-optic light port 62. In a preferred embodiment, the handset is ergonomically designed to fit into the surgeon's hand when gripped. However, this is not a limitation on the present invention. Preferably, handset 60 is made of a metal, such as stainless steel or titanium. However, it can be made of other materials, such as a plastic or the like. As is described below, instrument port 64 is compatible with a number of the instruments that are used in the inventive surgical procedure. The design structure and form allows right to left hand interchangability with ease and precision.

In a preferred embodiment, instrument dock 64 includes an inner threaded surface or threaded female connector 66 and a larger male connector 68 that interlocks with the skin ports 80 (described below) allowing deployment and illumination. The instrument dock 64 is adapted to dock with certain instruments, as will be described more fully below. Handset 60 will be described more fully below in conjunction with the instruments with which it is intended to be used.

The fiberoptic light port 62 allows docking with a fiberoptic light cord (not shown). The transmission of fiberoptic light through the handset 60 illuminates each device when it is attached to the working end of instrument dock 64.

In a preferred embodiment, the handset 60 includes a fiberoptic core 70, which is made up of at least one, and preferably a plurality, of fiberoptic strands. When a fiberoptic light cord is connected to light port 62, the light is transmitted through the fibers and out through an opening 72 that is coaxial with female connector 66.

In another embodiment other types of lighting can be used. For example, LED, incandescent, fluorescent and other light sources can be used. However, it will be understood that the light transmission is not a limitation on the invention. The handset 60 (and associated instruments) can be provided without a fiberoptic core.

Referring to FIGS. 28-34, another embodiment of a handset or lighting device 360 is shown. In a preferred embodiment, handset 360 is battery operated and disposable.

Figure 29:
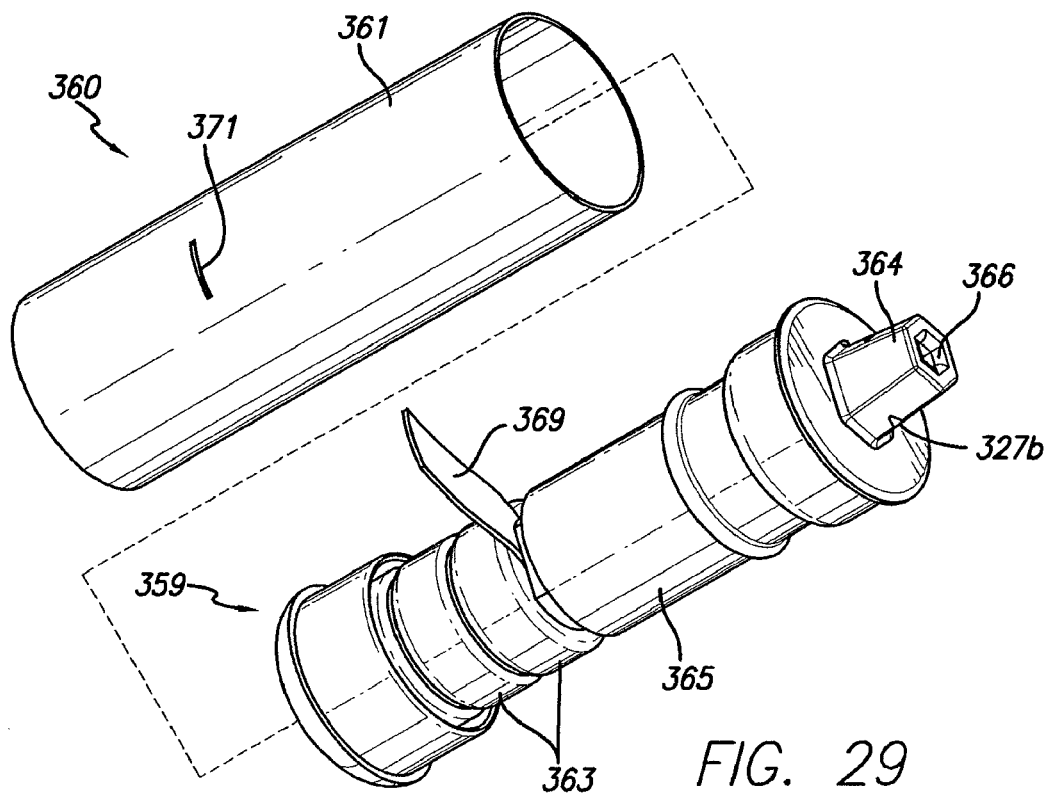
FIG. 29 is an exploded perspective view of the handset of FIG. 28.
Figure 30:
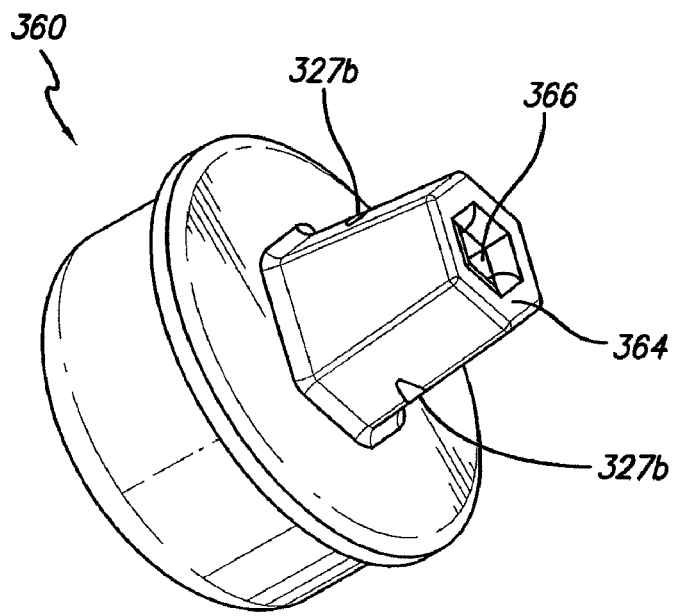
FIG. 30 is a detailed perspective view of the instrument dock of the handset of FIG. 28.
Figure 31:
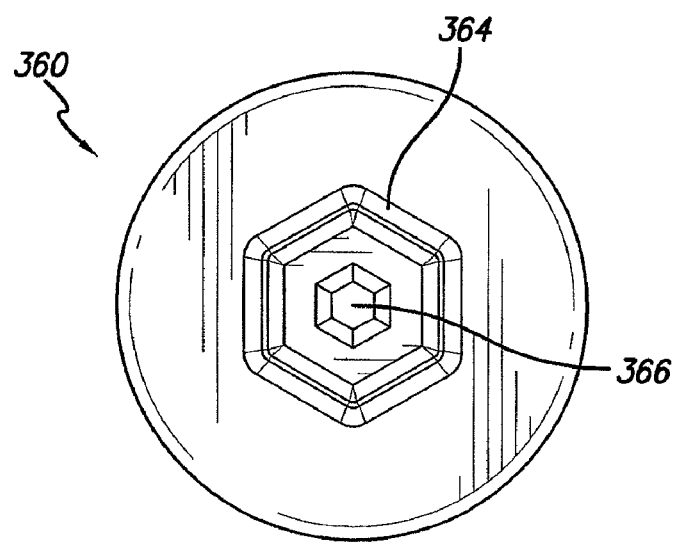
FIG. 31 is an end view of the handset of FIG. 28.

As shown in FIG. 29, the handset includes a main body portion 359, housing 361, power source(s) 363, light source 365, instrument dock 364 and an obturator or clearing device 321 (described more fully below). Preferably the light source 365 is an LED light source 365*a* and the power source 363 includes a plurality of batteries 363 arranged in series in housing 361. The circuitry for providing power to the light source is well known in the art and therefore a description will be omitted. In a preferred embodiment, the handset (in particular, the housing 361) is generally tubular. In other words, it does not have to have a circular cross-section; it may be square, oval or other shape.

In a preferred embodiment, the handset 360 is provided with the batteries 363 therein. In this embodiment, something is used to break the circuit so that the batteries are not drained prior to use. For example, a thin piece of paper or the like (referred to herein as a rip cord or circuit breaker 369) can be inserted between two batteries 363 to keep the circuit open and is then removed at the appropriate time to allow electrical communication between the batteries, thereby closing the circuit and lighting the light source 365. As shown in FIG. 29, the housing preferably has a slot 371 defined therein through which rip cord 369 extends.

In use, when the surgeon is ready to use the handset 360, he/she pulls the rip cord to power the LED 365a and it will then run for a predetermined amount of time (e.g., until the batteries die). It will be understood that handset 360 can also be constructed so that it is reusable. For example, those skilled in the art will understand that it can be designed to be plugged into a typical wall outlet and run on AC power.

In a preferred embodiment, the power source and light source are sealed off from the outside of the handset 360. This helps with sterilization and prevents contamination of the working area.

Figure 46:
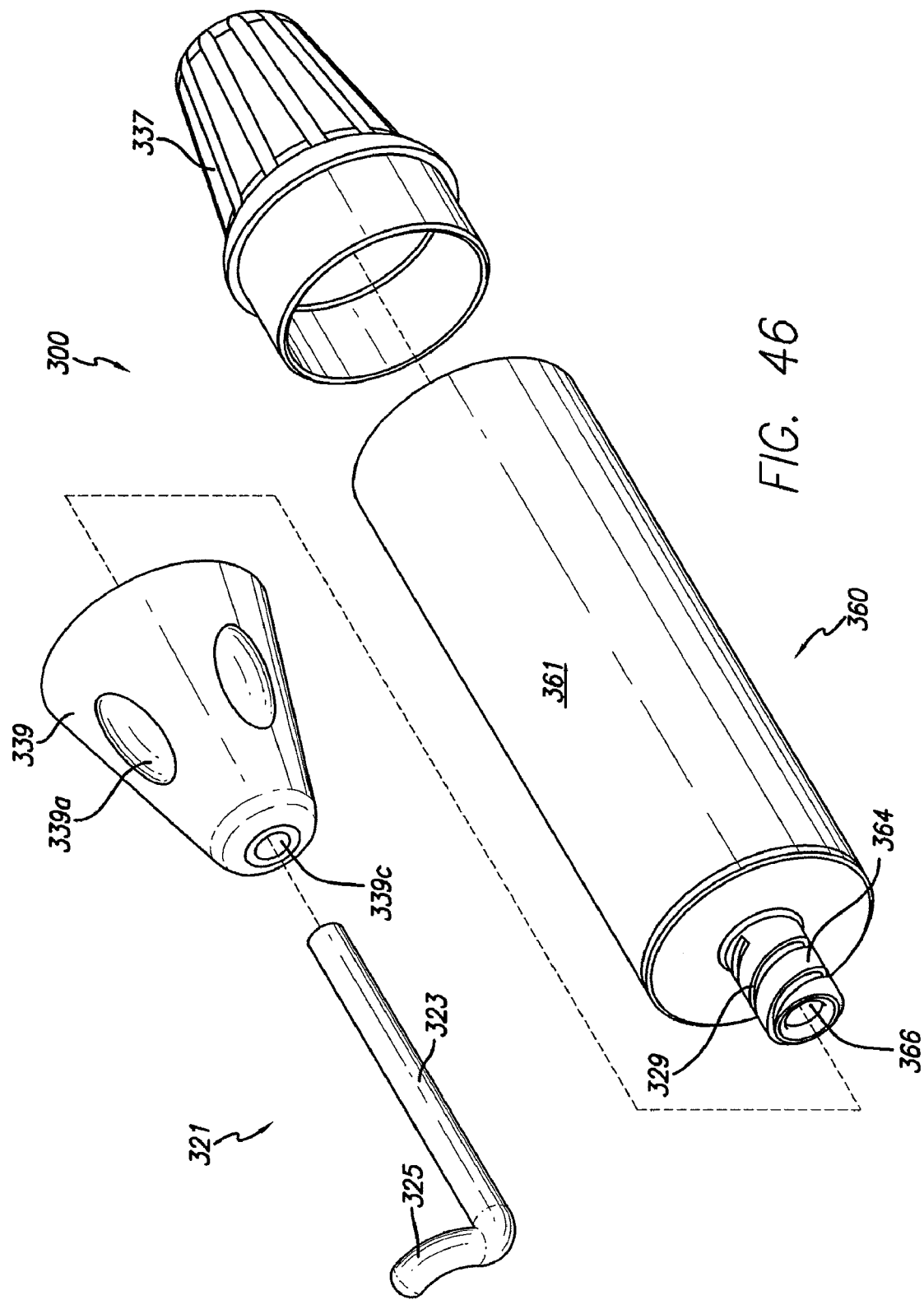
FIG. 46 is an exploded perspective view of a handset and clearing device in accordance with another preferred embodiment of the present invention.

In another preferred embodiment, instead of using a rip cord, a latching switch mechanism can be used for activating the batteries or turning on the light source. Any method for switching the latching switch mechanism on is within the scope of the present invention. For example, as shown in FIGS. 46 and 47, the handset 360 can include a tail cone or button 337 that can be twisted or pressed to switch the device on. Or, a switch can be located inside female receiver 366. In this embodiment, when clearing device 321, clearing device assembly 341 or threading rod 300 (described below) are inserted into the receiver 366, the switch is switched and the batteries and LED are activated. For example, the ring located next to o-ring 335 in FIG. 46 could be coupled to a magnetically activated switch.

Instrument dock 364 and clearing device 321 are described more fully below.

FIGS. 8-11 show a skin port 80. In a typical procedure, a plurality of skin ports 80 are used. In a preferred embodiment, skin ports 80 are disposable clear plastic sleeves that are each inserted into one of the access sites 14 created by lancet 40.

Generally, skin port 80 includes a flange or cuff 82 that has a tube 84 that extends from it. One end of the tube or sleeve 84 is inserted into the puncture 14 in the skin until the flange 82 rests against the outer surface of the skin. The flange 82 and tube 84 cooperate to define a tunnel 86 that will provide access to the area under the skin. Preferably, the port 80 is comprised of colored clear plastic. However, the port 80 can also be made of other materials, does not have to be clear and does not have to be colored.

In a preferred embodiment, the handset 60 or 360 is used to deploy each port 80 through the individual access sites 14. Preferably, the skin ports 80 come in a kit, however this is not a limitation on the present invention. The handset 60 design allows quick interlocking with the skin port 80 to remove it from the kit. It will be understood that any design that allows the handset 60 to interlock with or engage the skin port 80 so that it can be deployed into the access site 14 is within the scope of the present invention.

In a preferred embodiment, the port 80 is snap fit onto the male connector 68. For example, as shown in FIG. 8, the male connector 68 can include a ridge 68a extending circumferentially therearound that cooperates with an indented ring 82a in the flange 82. The ridge 68a and indented ring 82a provide a snap fit so that the port 80 is engaged with the male connector 68 of the handset 60. Other snap fit arrangements are contemplated.

The tube 84 is then inserted through the access site 14. As shown in FIGS. 8-11, in a preferred embodiment, the skin port 80 includes an anchor system that comprises threads 88 on the outer surface of the tube 84 and a folding mechanism 90. The folding mechanism 90 preferably includes a pair of folding members 90a that are attached to an internally threaded ring 90b that moves up and down the tube 84 on threads 88.

Figure 11:
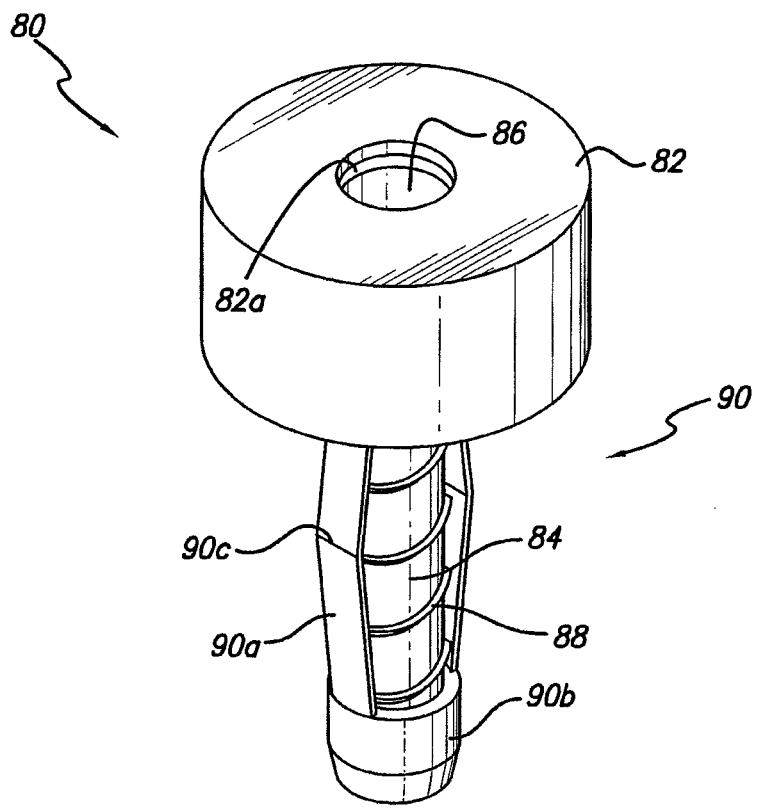
FIG. 11 is a perspective view of the skin port.

As is shown in FIG. 8, the male connector 68 includes a plurality of teeth 68b on an end thereof that are adapted to interlock with teeth 82b on the port 80. When the port 80 is engaged with the instrument dock 64, teeth 68b engage or mesh with teeth 82b. After the tube 84 has been inserted through the access site 14, to deploy the folding mechanism 90, the handset 60 is turned in a clockwise direction (port 80 can be designed to deploy in a counter-clockwise direction as well). Because teeth 68b and 82b are engaged, the tube 84 turns with handset 60 and within flange 82, thereby causing the internally threaded ring 90b to move upwardly along threads 88. As can be seen in FIG. 11, folding members 90a include a fold crease 90c. As threaded ring 90b moves upwardly, the folding members 90a fold, as shown in FIG. 10, thereby providing an anchor and preventing port 80 from pulling out of access site 14. The folding members 90a can be disposed in an unfolded position (FIG. 9) and a folded position (FIG. 10).

In a preferred embodiment, flange 82 includes a plurality of spikes 94 extending downwardly therefrom that burrow into the skin and help anchor the port 80 in place.

During placement of the port 80, because the handset 60 includes the fiber optic core 70 and the skin port 80 is clear, upon insertion, transcutaneous visualization of the lighted probe tip will allow safe deployment of skin port 80. Because of the anchoring system, as the handset is withdrawn, the ridge 68a pulls out of the indented ring 82a and the skin port 80 is secured in place. In another embodiment, the surgeon can use his/her thumb to aid in separating the port 80 from the instrument dock 64.

Preferably, the ports 80 are disposable and are only used for a single surgery. It will be understood that the ports are simply used to gain access to the surgical field. Therefore, the type of port used is not a limitation on the present invention. Any type of port that provides access through the skin is within the scope of the present invention. The transillumination of light gives three dimensional feedback to the surgeon.

Figure 12:
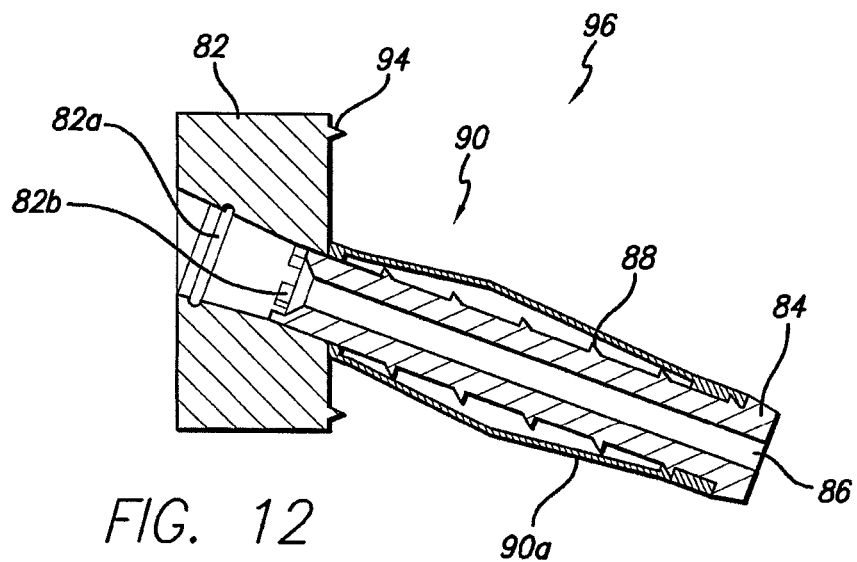
FIG. 12 is a cross-sectional view of another embodiment of a skin port.
Figure 13:
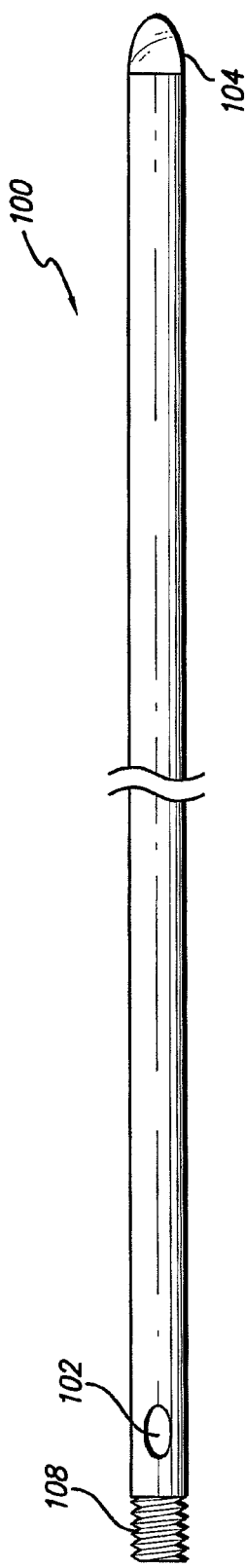
FIG. 13 is a side elevational view of a threading device in accordance with a preferred embodiment of the present invention.
Figure 14:
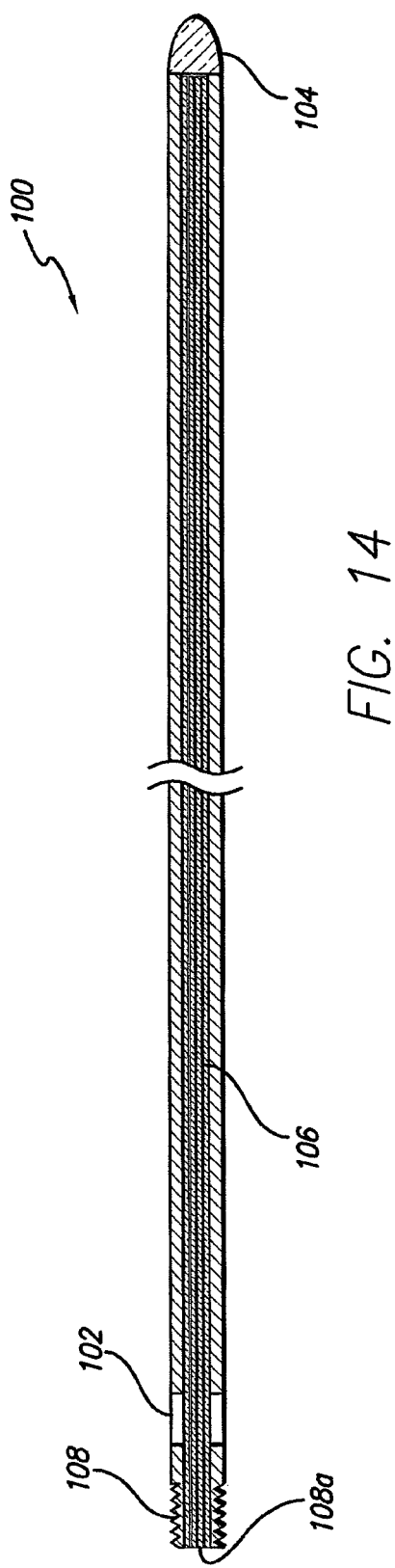
FIG. 14 is a sectional side elevational view of the threading device of FIG. 13.

As shown in FIG. 12, in an alternative embodiment, port 96 can have a tube 84 that is oriented at a non-right angle with respect to the flange 82. For example, tube 84 can be oriented at a 45 degree angle with respect to the flange.

FIGS. 13-17 show a preferred embodiment of a threading device 100. In a preferred embodiment, threading device 100 is a stainless steel malleable rod or tube that includes an eyelet 102 defined therein and a rounded, blunt tip 104. Preferably, threading device 100 also includes a light guide (which may be a fiberoptic core) 106 allowing illumination of tip 104. In this embodiment, the tip 104 is preferably made of a translucent material, such as a plastic that is affixed to the main body of the threading device 100. Threading device 100 includes an end 108 that is designed to dock with instrument dock 64 or 364 of handset 60 or 360. In a preferred embodiment, end 108 is threaded for engagement with female connector 66, however, it will be appreciated that end 108 can dock with instrument dock 64 in a number of different ways. For example, instrument dock 64 can include a set screw that holds threading device 100 in place or some type of snap or press fit can be provided. In another embodiment, a clamp or chuck, similar to that on a drill can be used. Also, end 108 can be internally threaded and can dock with an externally threaded instrument dock. Instrument dock 64 allows quick connection and disconnection with threading device 100.

In an embodiment where handset 60 includes a fiber-optic light port 62, docking of end 108 (which includes an opening 108a therein) with instrument dock 64 allows the transmission of light to tip 104 of threading device 100. In another embodiment other types of lighting can be used. For example, LED, incandescent, fluorescent and other light sources can be used.

It will be understood that, eyelet 102 is used to secure the suture 150. Eyelet 102 can be located anywhere along threading device 100.

In use, threading device 100 (and suture 150) are inserted through the various skin ports 80 and the support matrix 200 is weaved and created.

Figure 52:
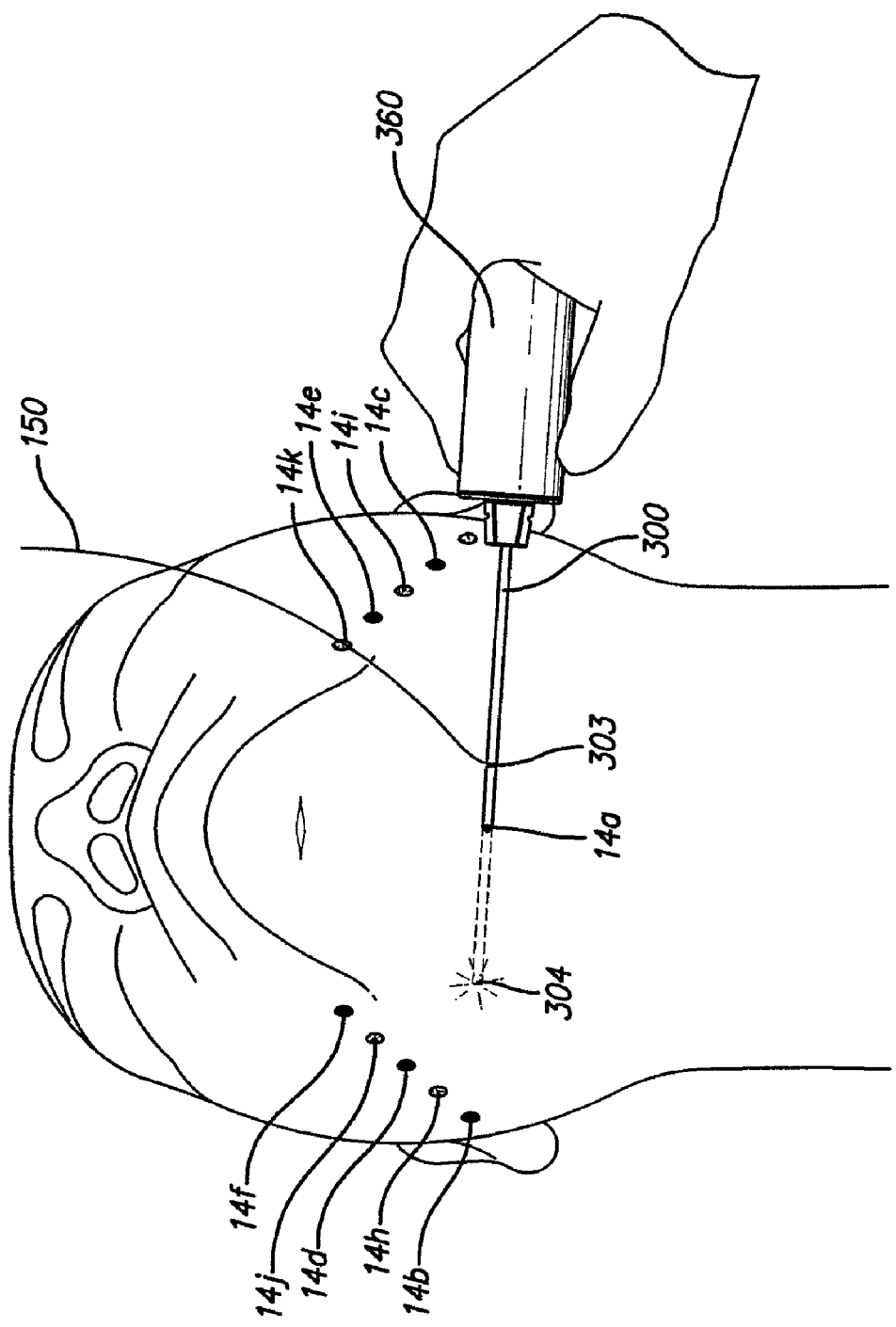
FIG. 52 is a view of a patient showing insertion of the threading rod and first suture into access site 14a using the handset.

FIGS. 36-45 show another embodiment of a threading device or rod 300 that includes eyelet 302 or groove 303 (referred to herein as a suture tie-off location) at a point that is about midway between the ends thereof. As shown in FIG. 52, in a preferred embodiment, suture 150 is tied around threading device 300 and is received in groove 303. Groove 303 is preferably defined circumferentially around the outside of device 300. However, in another embodiment, the groove only extends partially around the device 300. The device 300 may also have a recess 305 defined therein in which the knot 150c is received. This reduces the profile of the knot 150c and helps prevent the knot 150c from catching on anything (ligaments, skin, suture, etc.) when threading device 300 is used.

Figures 37, 38:
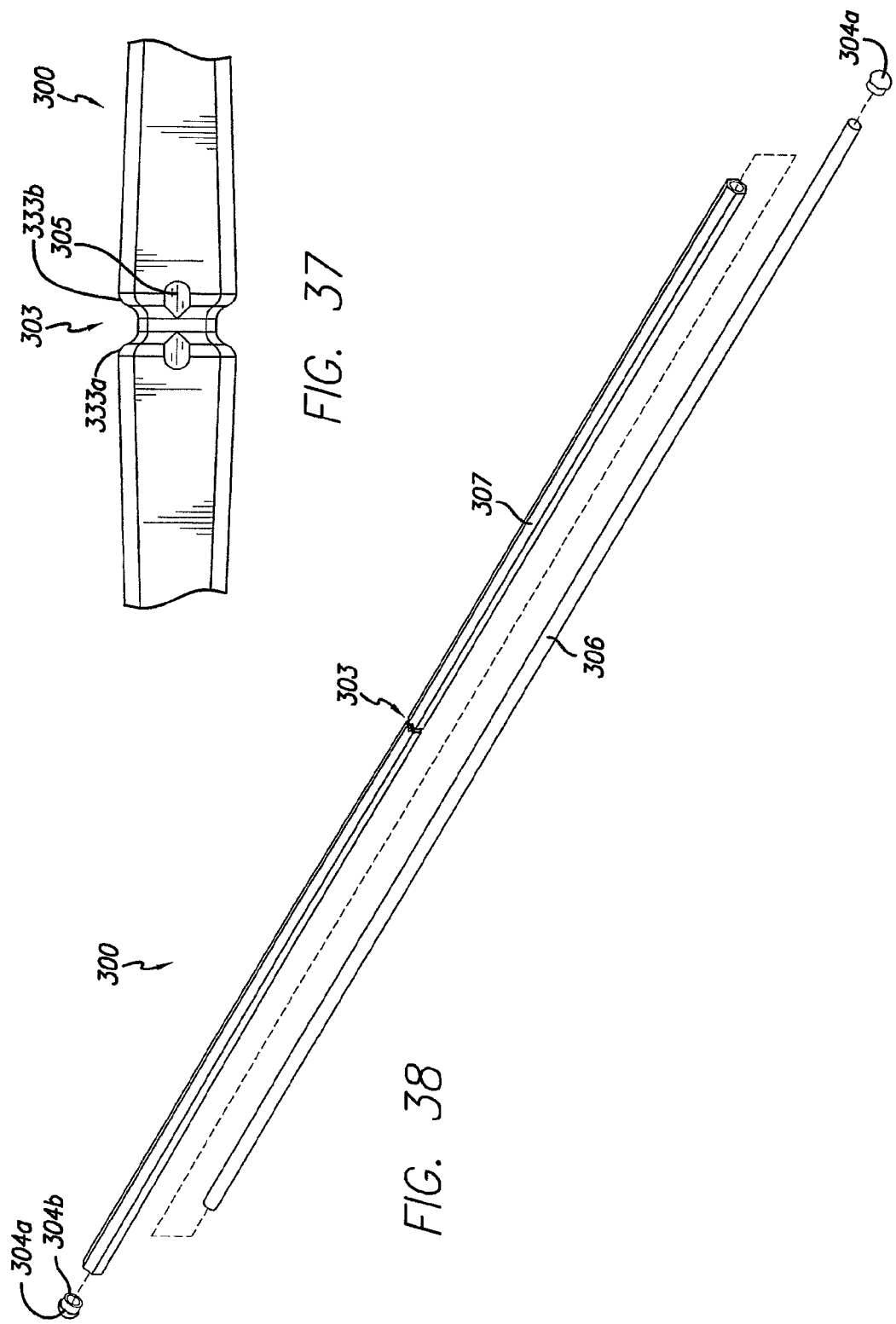
FIG. 37 is a detailed elevational view of a portion of the threading device of FIG. 36 showing that it is tapered.
FIG. 38 is an exploded perspective view of the threading device of FIG. 36.

As shown in FIG. 38, in a preferred embodiment, threading device 300 includes opposite ends or tips 304, tube 307, end caps 304a and light guide 306. In another embodiment, threading device 300 is solid. In yet another embodiment, the tips and light guide can be integral or the tips can be omitted. The threading device 300 can be solid metal with no lighting capabilities or can be formed completely of a solid (or plurality of components) made of a translucent or light conducting or transmissive material (such as plastic) so that the entire device lights up and/or so that the device is more flexible and easier and cheaper to manufacture. It will be understood that in a preferred embodiment, that the ends or tips of the threading rod 300 are blunt. As used herein, blunt means that the ends do not puncture the skin or any other part of the patient's anatomy without sufficient force (a force above that typically used in the procedure described below). As those skilled in the art will understand, a typical suture needle punctures the skin with very little pressure or force applied to it. The blunt ends of the present threading device 300 (whether flat or convex) do not puncture the skin when used as described below. However, in another embodiment, the ends can be sharp.

In the embodiment with the eyelet, eyelet 302 may formed so that when the knot 150c is tied therethrough, it is received in a recessed portion (now shown, but similar to recess 305).

In yet another embodiment, a suture 150 and threading device 300 can be formed as a unit. In other words, the suture 150 is permanently attached to the threading device 300 and the two can be provided to a surgeon as a unit.

Preferably, threading device 300 is malleable. For example, tube 307 can be made of stainless steel, titanium or other metal and light guide 306 can be made of a plastic (e.g., acrylic, styrene, polycarbonate or the like) or glass.

Figure 39:
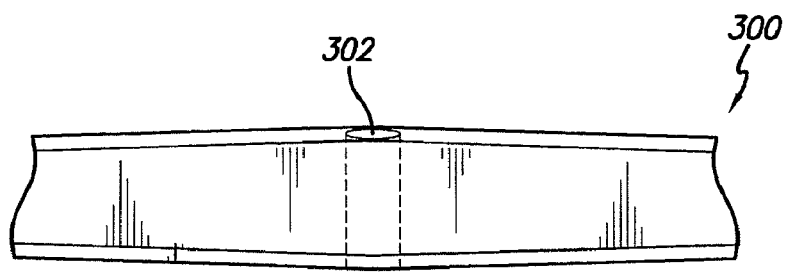
FIG. 39 is a detailed elevational view of a portion of a threading device that includes an eyelet.

In another preferred embodiment, to make threading device 300 even more malleable (and easier to insert into the access sites 14), tube 307 can be tapered (or the entire device 300 can be tapered in the case of a solid rod) from the ends to groove 303, eyelet 302 or suture tie-off location (as shown in FIGS. 37 and 39). In another embodiment, as is best shown in FIGS. 41 and 49, the rod tapers from a first location 333a to the left of the groove 303 toward the first end and the rod tapers from a second location to the right 333b of the groove 303 toward the second end. Therefore, the rod has a smaller diameter at the first and second ends than it does at the first and second locations. As is shown in FIGS. 41-42, excluding groove 303, the area between first and second locations 333a and 333b has a constant diameter. This prevents stress concentration in the center of the rod 300 and helps prevent failure of the rod during use. It will be understood that the first and second locations 333a and 333b can be located anywhere along the length of rod 300.

As shown in FIG. 36, in one preferred embodiment, threading device 300 is non-round. For example, it may be hexagonal. In this embodiment, a female receiver 366 of instrument dock 364 of the handset 360 or 60 has a corresponding shape. This prevents threading device 300 from rotating when docked. In another embodiment, only the ends of threading device 300 are polygonal. It will be understood that any way for keying the threading rod and preventing it from rotating is within the scope of the present invention. To also help prevent threading device 300 from being pulled out of female receiver 366, the instrument dock can have an elastomeric o-ring 335 therein that provides a friction fit with anything inserted therein.

As shown in FIG. 38, tube 307 is hollow and light guide 306 runs through it. In one preferred embodiment, the ends 304 of tube 307 are preferably capped by end caps 304a. End caps 304a are preferably hollow, made of a transparent plastic and preferably include a flange 304b that is received in tube 307 in a press fit arrangement. Caps 304a can also be threaded or glued into the ends of tube 307. In a preferred embodiment, end caps 304a are bullet-shaped and provide total internal reflection.

As shown in FIGS. 41-43, in another preferred embodiment, tube 307 is round, and light guide 306 is flush with the ends 304 of tube 307, and the recess described above is omitted. This embodiment also includes the taper locations 333a and 333b described above. However, locations 333a and 333b can be omitted, therefore, providing the tube 307, excluding groove 303 with a constant diameter. In this embodiment, the caps 304a are omitted. To secure the light guide 306 in tube 307, the light guide 306 can be potted, which is an adhesive that fills the space between the light guide 306 and the inner diameter of the tube 307. It will be understood that the entire light guide 306 or just the ends can be potted. In this embodiment, the ends 304 of the rod 300 may be ground, polished and buffed to promote light transmission and to make the ends of tube 307 and light guide 306 flush, as shown in FIG. 43. The ends 304 can be flat or convex.

As will be appreciated by those skilled in the art, in a preferred embodiment, to promote total internal reflection in the light guide 306, the light guide 306 can be cladded. If a plastic light guide is used, the outside of the light guide 306 can be cladded. If a glass light guide is used, as is known in the art, the glass billet can be cladded before the glass light guide is drawn. The use of cladding is not a limitation on the present invention, however, if it is not used, the potting compound may detract from the light transmission and make it less efficient.

When threading device 300 is docked with handset 360, light is transmitted through one end 304 of rod 300, through light guide 306 and out the other end 304. In a preferred embodiment, the bottom of female receiver 366 has a complementary shape to that of the ends 304, thereby providing efficient light transmission.

In a preferred embodiment, a high efficiency white LED is used. In this embodiment, the lighting device 360 may include a DC to DC converter to boost the voltage to the desired level for the high efficiency white LED.

It will be understood by those skilled in the art that it is desired that the light emitted by the LED is concentrated and emitted at a narrow angle of focus. In a preferred embodiment, the numerical aperture of the light guide 306 is matched as closely as possible by the light emitted from the LED. This helps maximize the efficiency of the light transmission.

Figure 40:
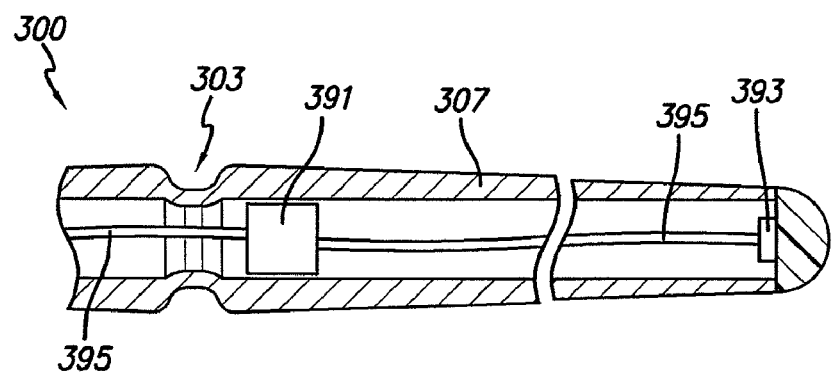
FIG. 40 is a cross-sectional partial elevation of a threading device with a self-contained power source and light source in accordance with another preferred embodiment of the present invention.
Figure 44:
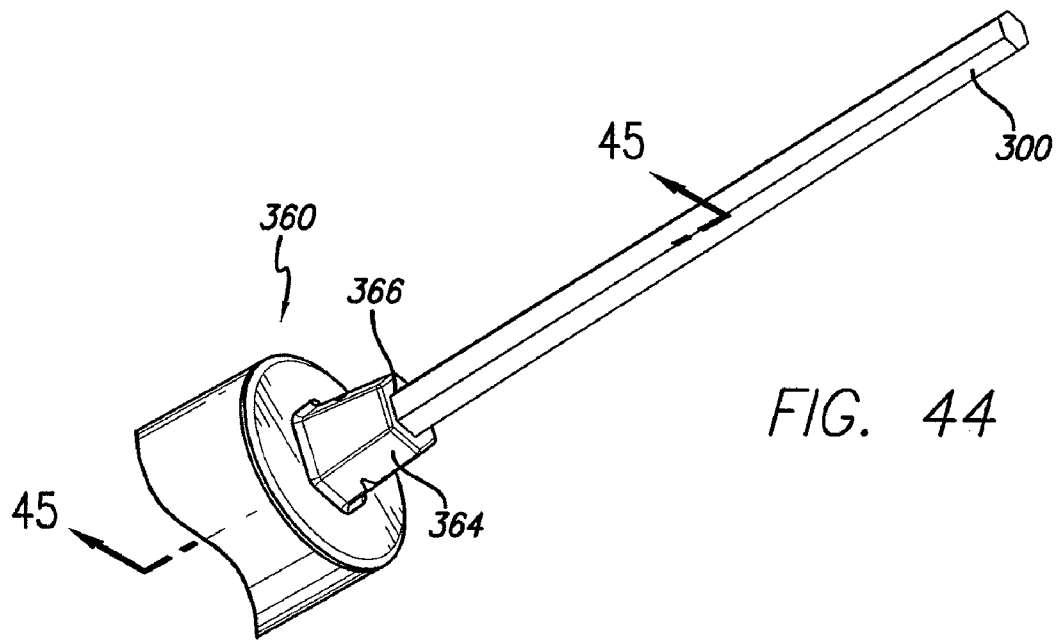
FIG. 44 is a perspective view of the threading device of FIG. 36 inserted into a handset.
Figure 45:
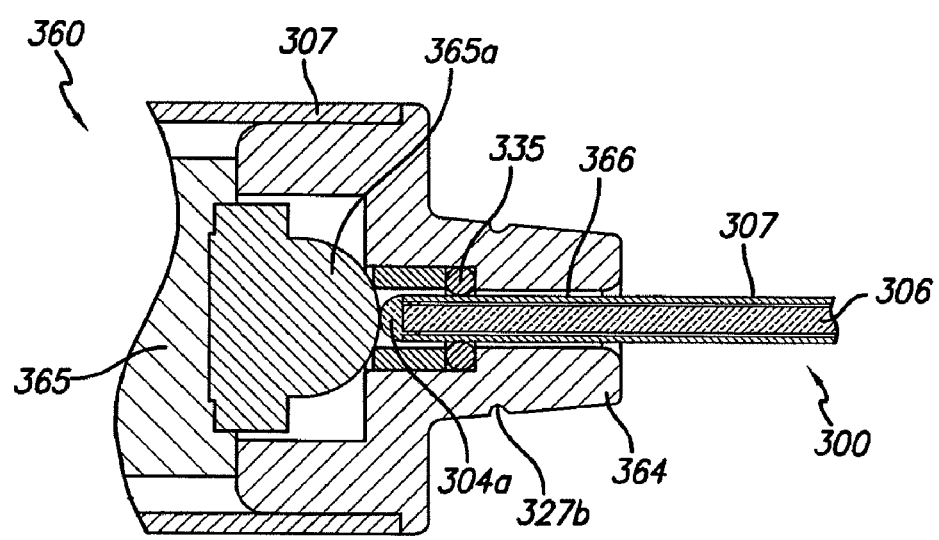
FIG. 45 is a cross-sectional elevation taken along line 45-45 of FIG. 44.

As shown in FIG. 40, in another embodiment, threading device 300 includes its own power supply 391 and light source 393. In an exemplary embodiment, the power supply 391 and light source 393 (e.g., LED's) can be connected by wires 395. In this embodiment, the handset can be omitted. For example, the threading device 300 can include an LED or the like at each end.

In another embodiment, the handset can reciprocate the threading device to help in passing the threading device subcutaneously. The reciprocating action allows the threading device to pass easily through fatty tissue, thus creating less collateral damage to blood vessels, nerve structures and other subcutaneous ligaments. This embodiment is similar to the device for reciprocating a cannula, which is described in U.S. Pat. No. 6,139,518 to Mozsary, which is incorporated in its entirety by reference herein. In this embodiment, the handset is powered to reciprocate the threading device back and forth during surgery. The threading device can be connected to the handle by a connector that is affixed to, integrally formed with, or selectively joinable to a reciprocating member. In another embodiment, the handset may reciprocate or vibrate the threading device ultrasonically.

FIGS. 33-35b show different embodiments of the clearing device 321, which is a blunt instrument for probing the puncture or access site and clearing ligaments and other obstructions. Generally, clearing device 321 includes a neck (also referred to as the docking portion) 323 and a clearing portion 325. Clearing portion 323 is preferably about the same diameter as threading rod 300, that way they both fit into the access sites.

Figure 33:
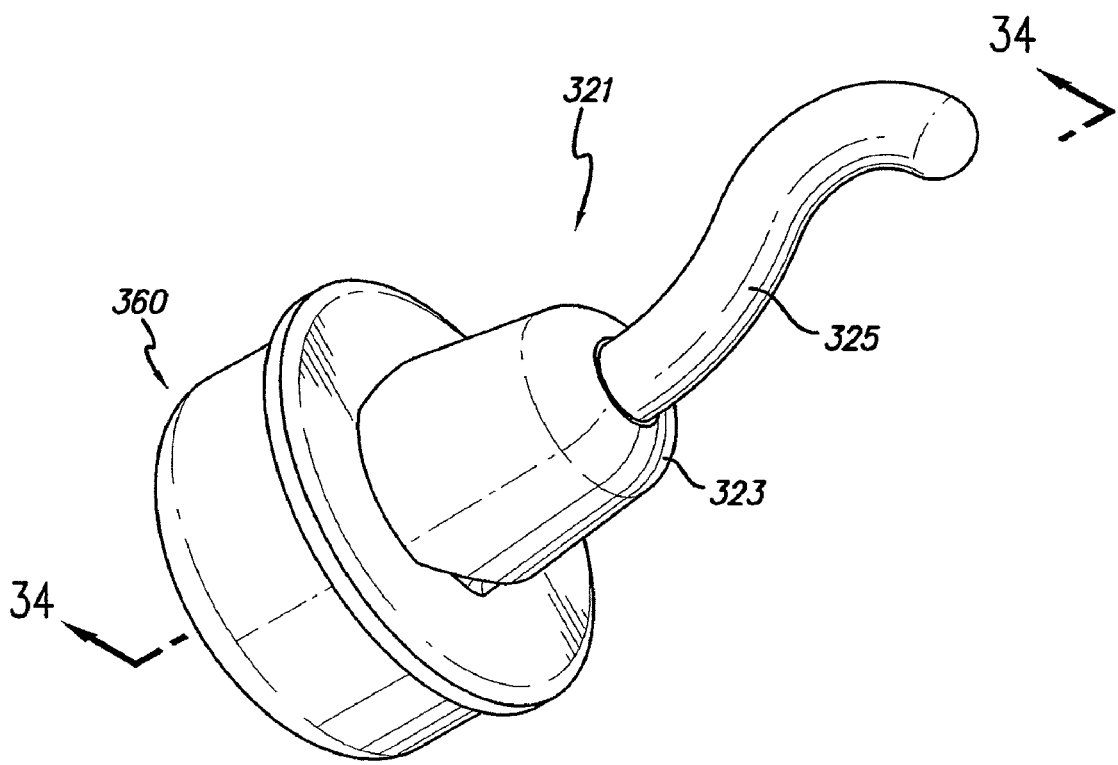
FIG. 33 is a perspective view of a clearing device secured on the end of the handset of FIG. 28.
Figure 34:
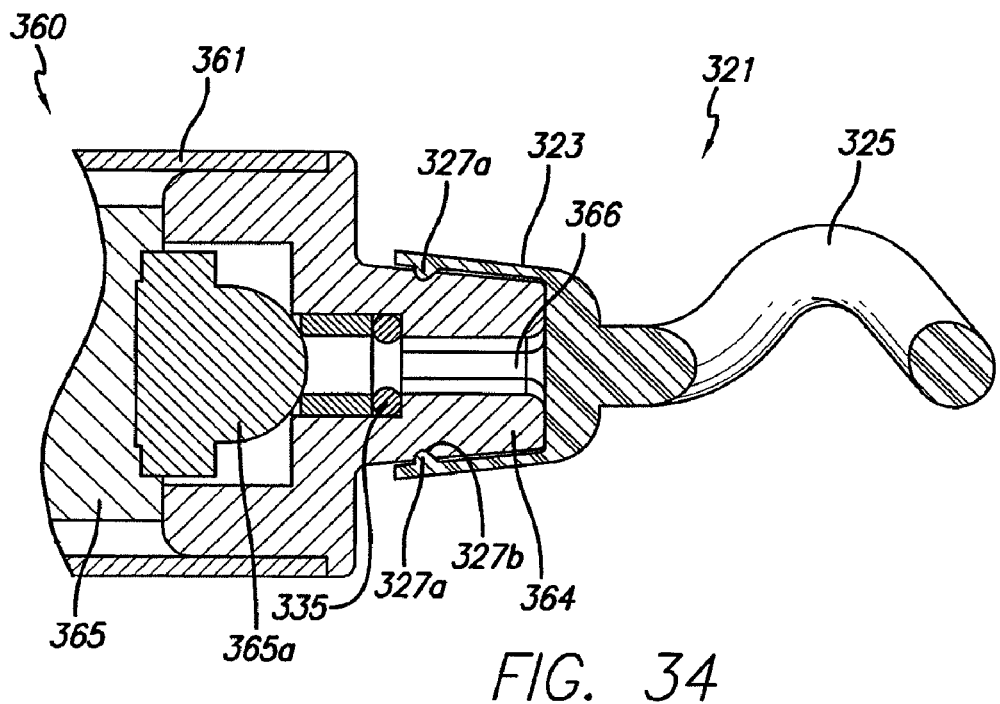
FIG. 34 is a cross-sectional view taken along line 34-34 of FIG. 33.

As shown in FIGS. 33-34, in one preferred embodiment, clearing portion 325 is spiral shaped. This allows the surgeon to insert the clearing portion 325 into the access site 14 and sweep the area under the access site clear by rotating the device (see FIG. 51 for a figure depicting use of the clearing device 321).

In a preferred embodiment, the clearing device 321 snap fits onto handset 360. To accomplish this, neck 323 and instrument dock 364 include corresponding protrusions 327a and indentations 327b, as best shown in FIG. 34. Clearing device 321 is preferably made of plastic, which allows flexibility for the snap fit arrangement, and also allows clearing device 321 to transilluminate. In use, light is emitted from instrument dock 364 and transilluminates the clearing device 321. In another embodiment, only the tip of the clearing device 321 is illuminated and the remainder of the device is opaque. This helps direct the light to the tip. In another embodiment, clearing device 321 can be made of metal.

Figure 32:
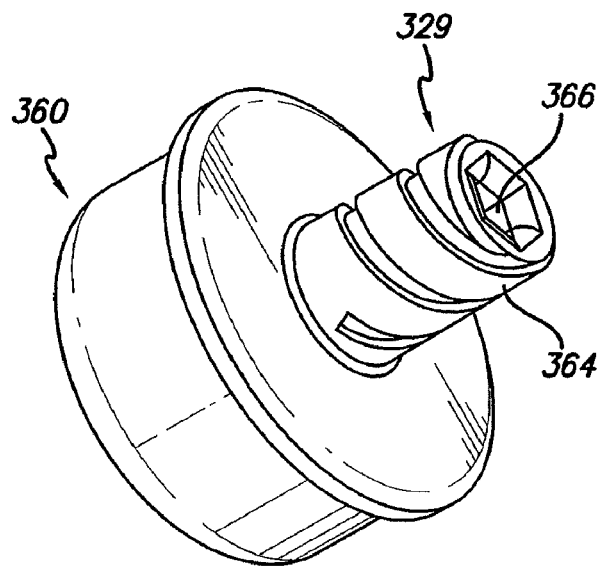
FIG. 32 is a detailed perspective view of another preferred embodiment of the instrument dock of the handset of FIG. 28.

It will be understood that clearing device 321 can be removably affixed to handset 360 in other ways. For example, an arrangement where a portion of neck 323 is received in slots on the handset 360 (or vice versa) and then the clearing device is turned and locked into place can be utilized. Also, as shown in FIG. 32, a threaded arrangement 329 is within the scope of the present invention. Clearing device 321 can also be designed to fit on handset 60.

Referring to FIGS. 46-47, another embodiment of a clearing device 321 is shown. In this embodiment, clearing device 321 can be a rod that fits in female receiver 366, as shown in FIG. 46. In this embodiment, the clearing device 321 includes a neck (or docking portion) 323 and a clearing portion 323. The neck 323 can be keyed (similar to the threading device, described below) to prevent rotation when inserted into female receiver 366.

Figure 35A:
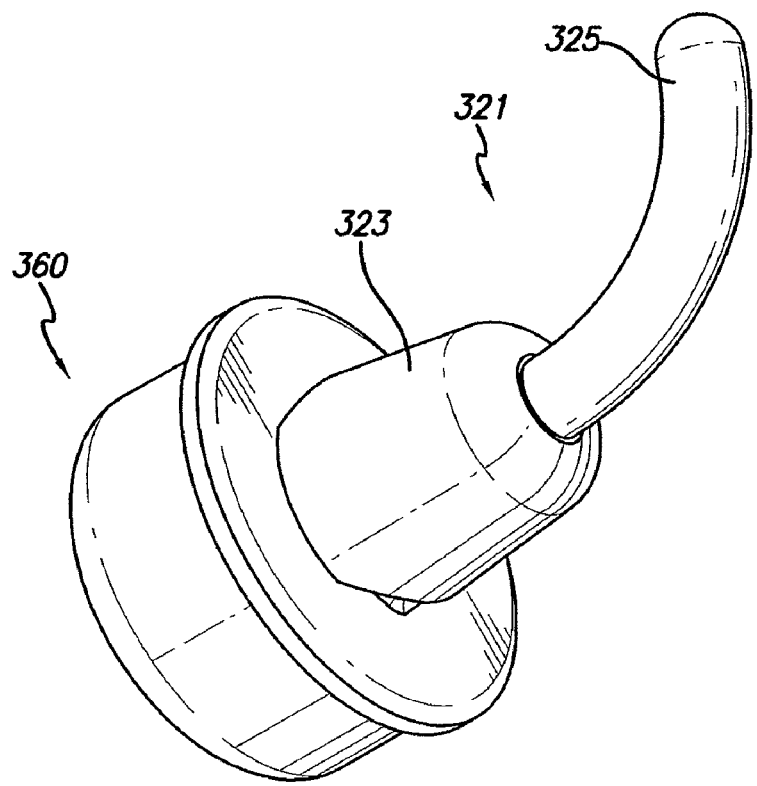
FIG. 35a is a perspective view of another clearing device secured on the end of the handset of FIG. 28.

FIGS. 35a and 35b show other embodiments of a clearing device with curved 325a and straight 325b clearing portions. These clearing portions can also be included on a clearing device that is received in female receiver 366 also.

Referring to FIGS. 46-49, another embodiment of a handset 360 is shown. The handset 360 is generally the same as described above. As is shown in the figures, the instrument dock includes threads 329 and a circular female receiver 366. The handset 360 can also include a tail cone 337 as described above. The tail cone 337 can simply be for providing the surgeon with something to grip when rotating the clearing device or can be designed to actuate a latching switch for actuating the light source, as described above.

In this embodiment, the device also includes a nose cone 339 that can be threaded on the instrument dock 364. The nose cone 339 preferably includes gripping indentations 339a and has an axial opening 339c defined therethrough that is axially aligned with female receiver 366 when nose cone 339 is threaded onto instrument dock 364. The nose cone 339 provides a grip for the surgeon when using the handset 360. This allows the surgeon to hold the handset similar to the way that one would hold a pen.

As shown in FIG. 46 (and as described above), the clearing device 321 can have a neck 323 that fits into female receiver 366 and that includes a clearing portion 325 extending therefrom. As shown in FIG. 47, in another preferred embodiment, the nose cone and clearing device can be formed as a unit, thereby creating a clearing device assembly 341. In this embodiment, the neck 323 is inserted into female receiver 366, while the nose cone 339 is threaded onto instrument dock 364 simultaneously. O-ring 335 helps secure neck 323 within female receiver 366. In this embodiment, clearing portion 325 extends in a curved path that defines a plane that is approximately perpendicular to the longitudinal axis of the neck.

As shown in FIG. 47, clearing device assembly 341 can include a light guide 306 extending therethrough for illuminating the tip. However, this is not a limitation on the present invention.

In a surgical procedure where clearing device assembly 341 is used, a separate nose cone 339b for securing threading rod 300, as shown in FIG. 48, is also preferably used. In use, after clearing device assembly 341 has been used to clear the area around the access sites, the clearing device assembly 341 is unscrewed from instrument dock 364 and then nose cone 339b is screwed on. Nose cone 339b includes an o-ring 335 therein for helping secure threading rod 300 when inserted into opening 339c and female receiver 366, as shown in FIG. 48. In another embodiment, nose cone 339b can be omitted. In yet another embodiment, nose cone 339b can include means for tightening the threading rod therein so that it is difficult to pull the threading rod out. For example, the nose cone 339b may include a set screw, chuck, interior threads or the like.

As shown in FIGS. 48 and 49, in another preferred embodiment, threading rod 300 can include securing channels 343 defined circumferentially therearound. When inserted into nose cone 339b or female receiver 366, one of the channels 343 receives o-ring 335, to help secure the threading rod 300 therein. The channels are located near both ends because the threading rod is reversible, as described below. In another embodiment, instead of an o-ring, the nose cone 339b or instrument dock 364 (see FIG. 50) may include a metal ring 345 that is received in the channels 343, which provides a stronger snap fit arrangement than the o-ring.

Figure 53:
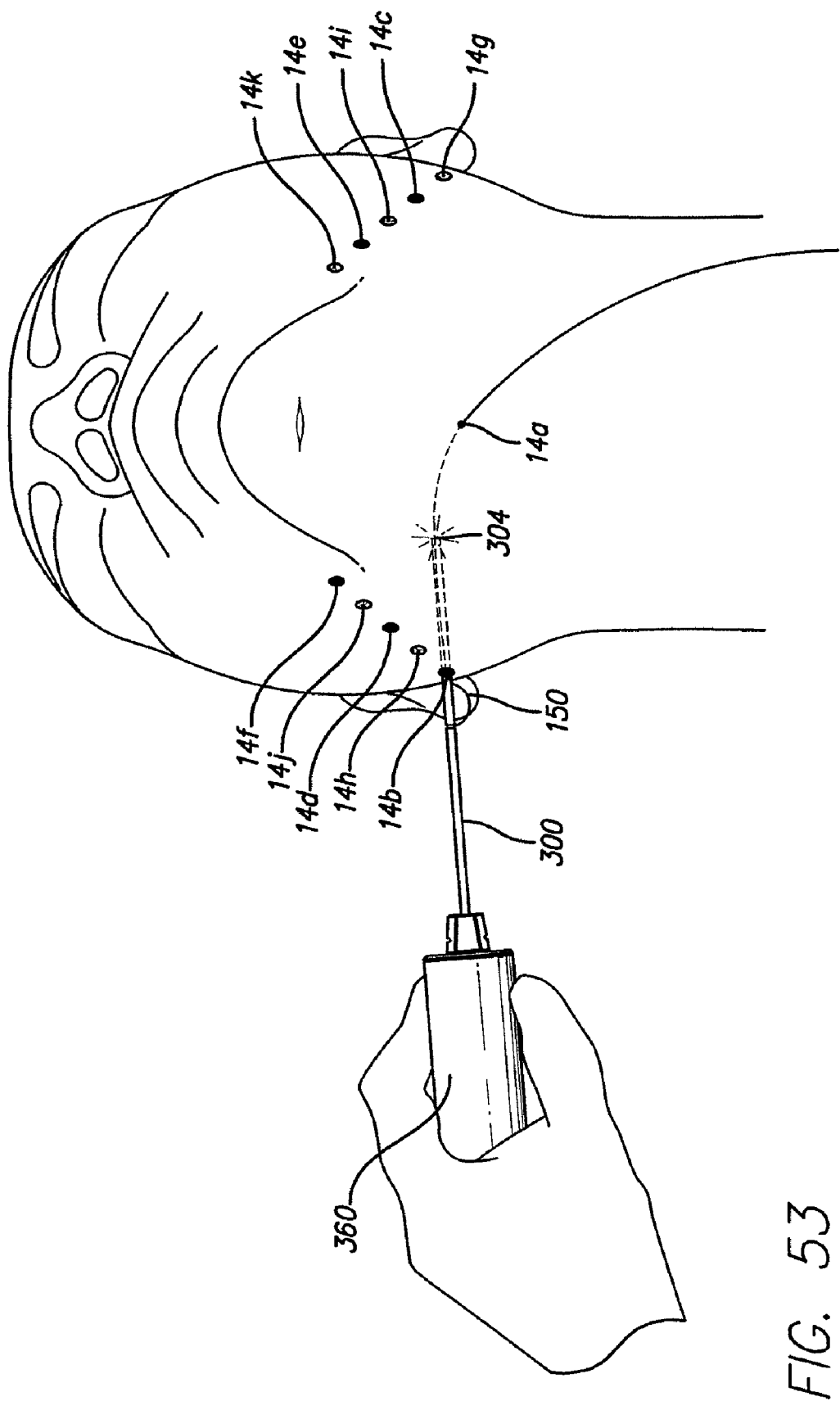
FIG. 53 is a view of a patient showing insertion of the threading rod and first suture into access site 14b after pivoting the threading rod.

It will be understood that the length of the threading rod 300 will change depending upon the type of procedure being performed (and the size of the patient's anatomy). It is important that the threading rod 300 be long enough so that as it is passed subcutaneously as one end emerges from an exit access site 14 that the other end extends out of the entry access site 14. For example, in the Percutaneous Trampoline Platysmaplasty, the threading rod 300 may be about nine inches long. With reference to FIG. 53, this allows one end of the threading rod 300 to extend out of access site 14*b* and the opposite end to extend out of access site 14*c* simultaneously. In the MACS-lift, the threading rod 300 does not have to be as long. It should be understood that the threading devices 100 and 300 shown in the figures are not to scale.

Figure 57:
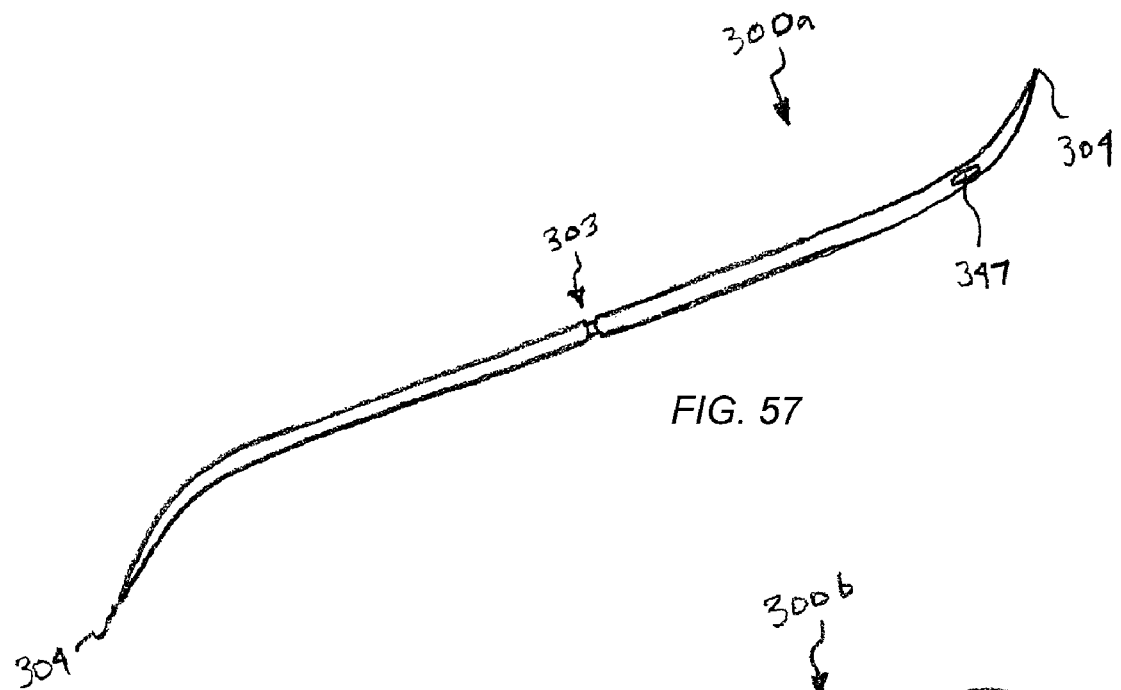
FIG. 57 is a side elevational view of a threading device in accordance with another preferred embodiment of the present invention.
Figure 58:
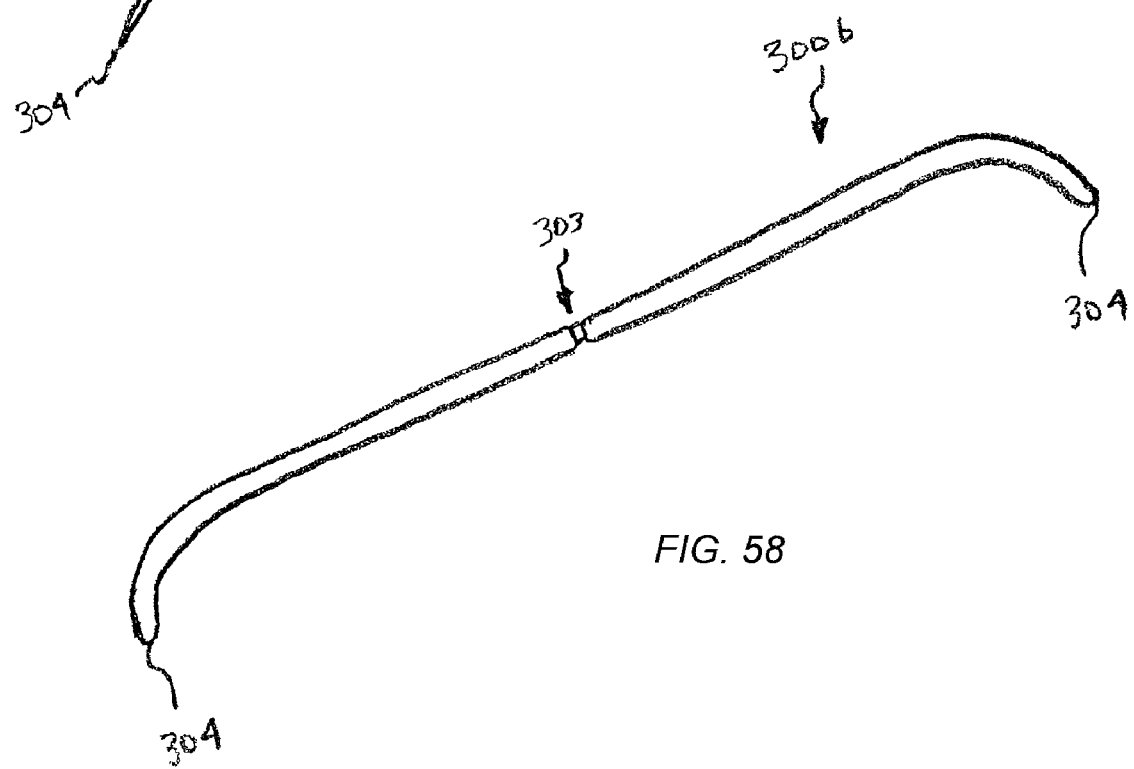
FIG. 58 is a side elevational view of a threading device in accordance with another preferred embodiment of the present invention.

With reference to FIGS. 57 and 58, in other embodiment, the threading rod can be curved or bent. For example, as shown in FIG. 57, the ends 304 can be curved in different directions. This type of threading rod 300*a* may be solid or may have a light guide therein. The ends can be sharp or blunt. In the embodiment with sharp ends, it may be difficult to transmit light through the ends 304, so an opening 347 can be made in the tube 307 to allow light to be emitted from a point spaced from the end 304. Threading rod 300*a* may be useful for abdominal surgery and may be thick and less malleable than the embodiments described above to strengthen the device. As shown in FIG. 58, in another embodiment, the threading rod 300*b* can have ends that curve in the same direction.

Figure 15:
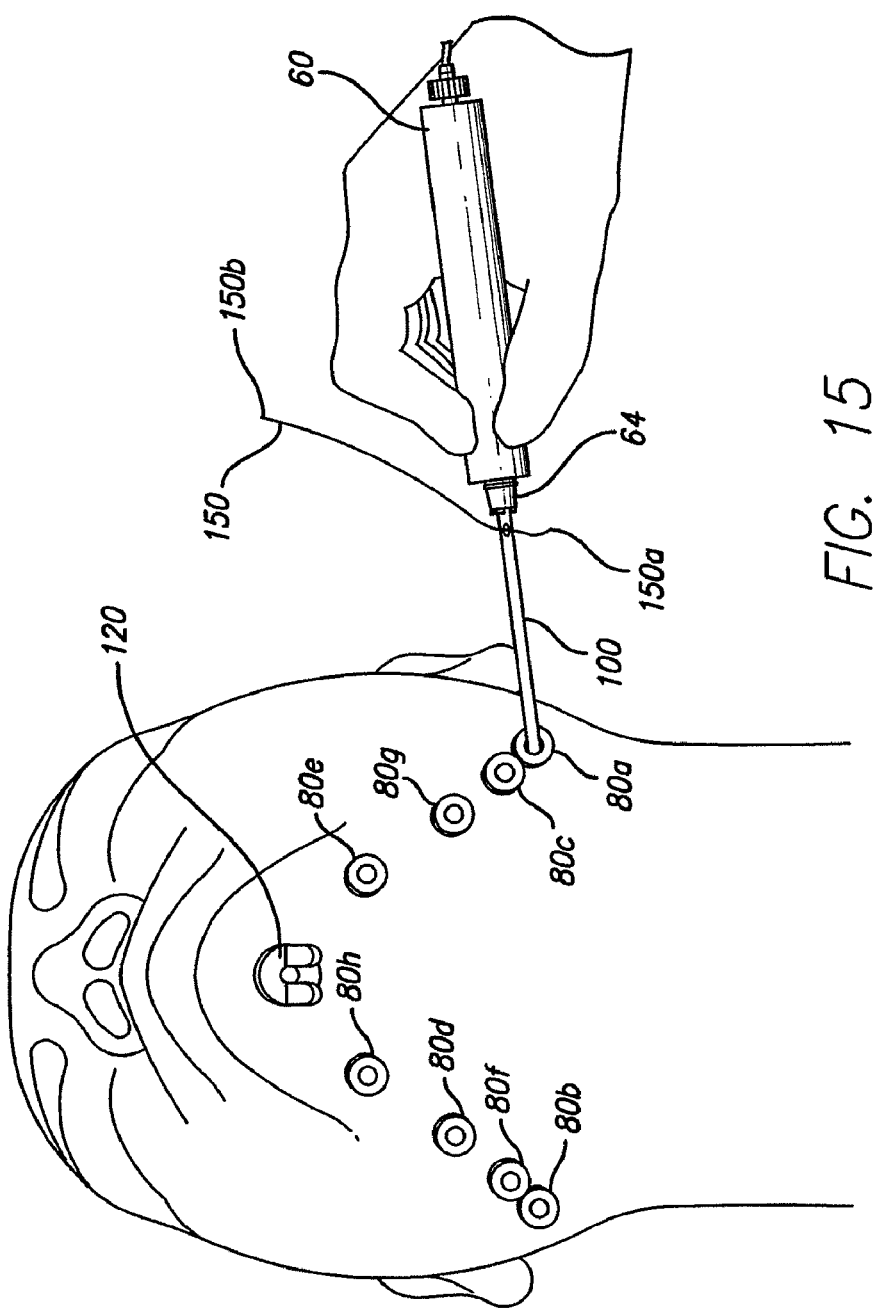
FIG. 15 is a view of the threading device of FIG. 13 being used on a patient.

An exemplary construction of a support matrix 200 using threading device 100 will now be described. For example, as shown in FIG. 15, after first end 150*a* of the suture 150 is connected to eyelet 102, the handset 60 is grasped by the surgeon and the threading device is inserted through a first skin port 80*a*. The lighted tip 104 of threading device 100 illuminates the work area and transilluminates through the skin allowing the surgeon to determine the proper placement of the support matrix 200 and the location of the tip 104. As described above, in a preferred embodiment, port 80 is clear for aiding in the passage of the threading device 100. In other words, when the tip 104 of threading device 100 gets close to port 80 it will transilluminate.

Figure 16:
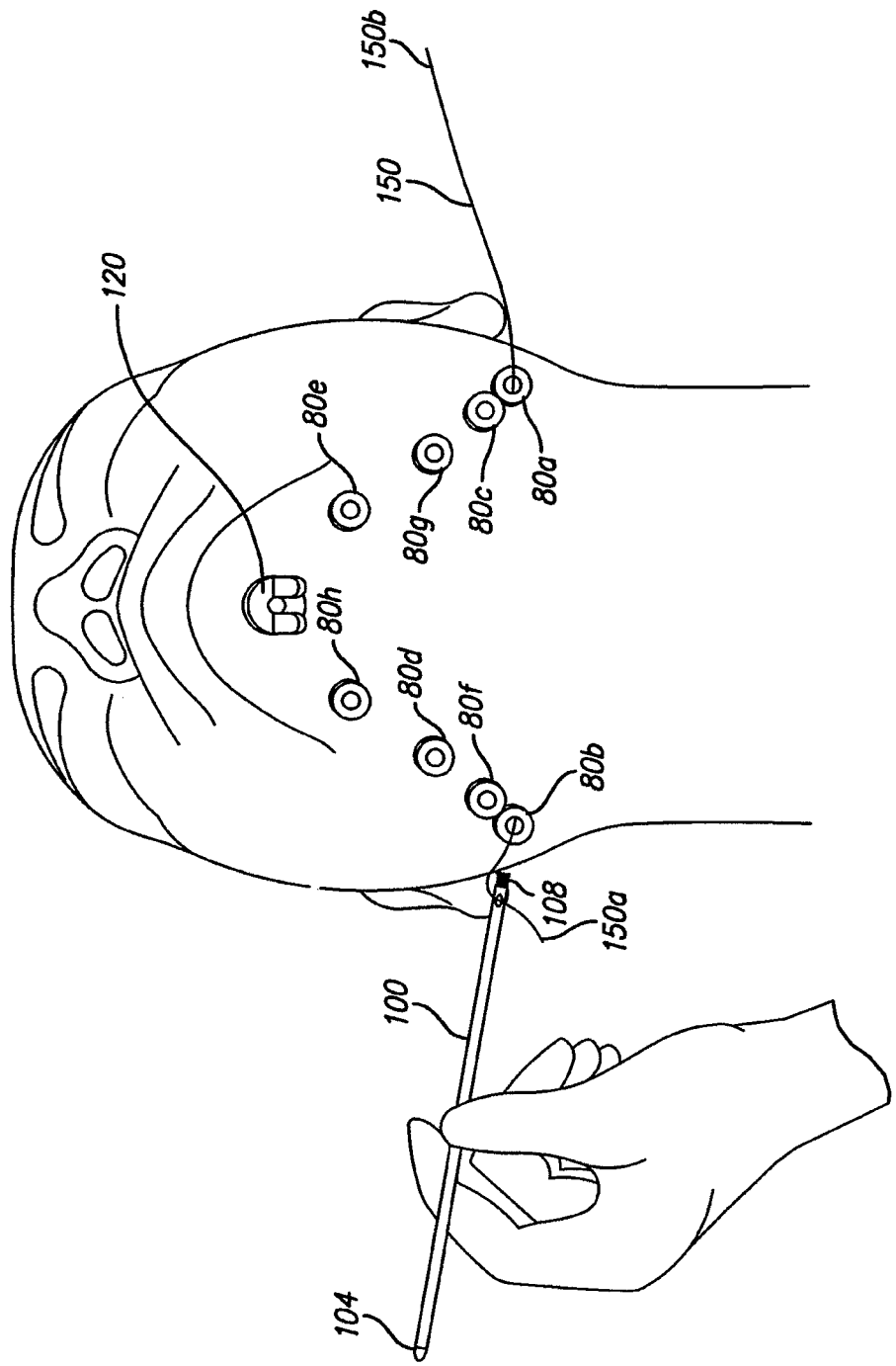
FIG. 16 is another view of the threading device of FIG. 13 being used on a patient.
Figure 17:
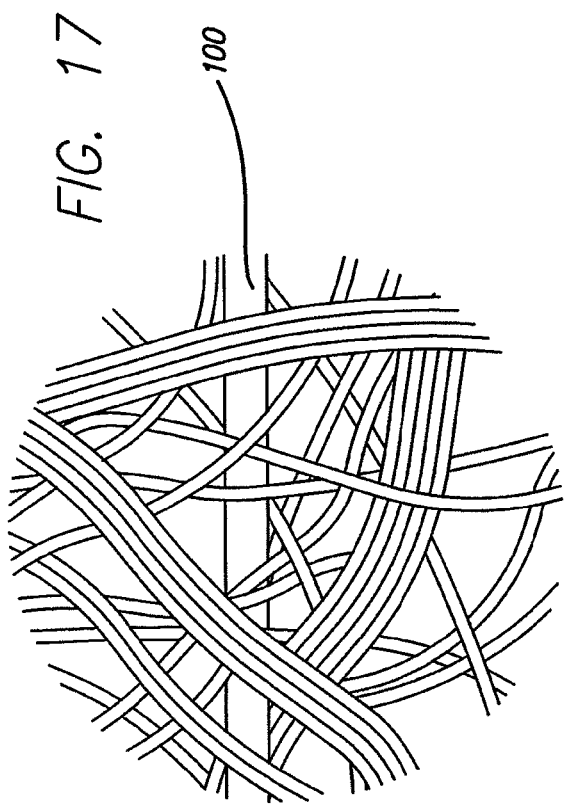
FIG. 17 illustrates the threading device of FIG. 13 passing through the subcutaneous facial ligaments and neurovascular structures.

The threading device 100 is preferably long enough that it can be threaded from one side of the jaw line to the other such that the tip 104 is brought out through a second skin port 80*b* on the opposite side of the jaw from which it was inserted. At this point, the tip 104 is grasped by the surgeon and the suture 150 is pulled through the area under the neck. Then the threading device 100 is disconnected from the handset 60 allowing the threading device 100 and the suture 150 to be pulled through the second skin port 80*b*, as is shown in FIG. 16.

The threading device 100 is then turned and reconnected to the handset 60 and is then reinserted through second skin port 80*b* and is passed subcutaneously to the contralateral side exiting through third skin port 80*c*. The threading device 100 is once again disconnected from the handset 60 and is reconnected after the threading device and suture 150 are pulled through third skin port 80*c*.

Next, the threading device 100 is turned and reconnected to the handset 60 and is then reinserted through third skin port 80*c* and is passed subcutaneously to the contralateral side exiting through fourth skin port 80*d*. At this point, the threading device 100 is once again disconnected from the handset 60 and is reconnected after the threading device and suture 150 are pulled through fourth skin port 80*d*.

The threading device 100 is then turned and reconnected to the handset 60 and is then reinserted through fourth skin port 80*d* and is passed subcutaneously to the contralateral side exiting through fifth skin port 80*e*. At this point, the threading device 100 is once again disconnected from the handset 60 and is reconnected after the threading device and suture 150 are pulled through fifth skin port 80*e*.

Next, the threading device 100 is turned and reconnected to the handset 60 and is then reinserted through fifth skin port 80*e* and is passed subcutaneously to the midline sub-mental access site which preferably includes a threaded skin port 120 (described more fully hereinbelow). The threading device 100 and first end 150*a* of suture 150 are pulled through the threaded skin port 122 and the threading device is disconnected from the handset 60. The first end 150*a* of suture 150 is then cut from and/or untied from the threading device 100.

Now, the second end (or distal end) 150*b* of suture 150, which is extending from first skin port 80*a* is secured to the eyelet 102 of the threading device 100 and the threading device 100 is connected to the handset 60. The handset 60 is grasped by the surgeon and the threading device is inserted through the first skin port 80*a* and is passed subcutaneously to the contralateral side exiting through sixth skin port 80*f*. At this point, the threading device 100 is once again disconnected from the handset 60 and is reconnected after the threading device and suture 150 are pulled through sixth skin port 80*f*.

Next, the threading device 100 is turned and reconnected to the handset 60 and is then reinserted through sixth skin port 80*f* and is passed subcutaneously to the contralateral side exiting through seventh skin port 80*g*. At this point, the threading device 100 is once again disconnected from the handset 60 and is reconnected after the threading device and suture 150 are pulled through seventh skin port 80*g*.

The threading device 100 is then turned and reconnected to the handset 60 and is then reinserted through seventh skin port 80*f* and is passed subcutaneously to the contralateral side exiting through eighth skin port 80*h*. At this point, the threading device 100 is once again disconnected from the handset 60 and is reconnected after the threading device and suture 150 are pulled through eighth skin port 80*h*.

Next, the threading device 100 is turned and reconnected to the handset 60 and is then reinserted through eighth skin port 80*h* and is passed subcutaneously to the threaded skin port 120 at the midline sub-mental access site. The threading device 100 and second end 150*b* of suture 150 are pulled through the threaded skin port 120 and the threading device is disconnected from the handset 60.

As will be understood by those skilled in the art, the tube 84 on the skin ports 80 is long enough that when the threading device 100 is inserted therethrough the suture 150 will anchor itself by encircling the facial retaining ligaments during the procedure described above. Preferably, each time the threading device 100 and suture 150 are passed through a port 80, the suture is secured on the facial retaining ligaments, thereby creating an anchor or pivot point.

It will be understood that the number of access sites 14, ports 80 and/or passes, etc. described above are merely exemplary and any number can be used in the presently described procedure, as required by the particular surgery.

Transcutaneous light transmission from the tip 104 of the threading device 100 gives feedback allowing the surgeon to determine the location of the tip 104 as the support matrix 200 is weaved and created. This feedback allows the placement of each individual strand relative to areas of needed support. This allows placement of the suture strands 150 adjacent to the muscle, deep to the skin and fat layers.

Preferably, in each port 80, the end of the tube 84 that is associated with the flange 82 has a beveled or tapered edge 84*a*, which helps prevent the tip 104 of the threading device 100 from catching inside the tunnel 86, during insertion.

In another embodiment, two threading devices 100 that are each connected to an opposite end of the suture 150 can be used. In this embodiment the first threading device 100 does not have to be disconnected from the end of the suture 150 before the second end of the suture 150 is threaded through the skin. In yet another embodiment, the suture 150 can come in a kit with two disposable threading devices 100 attached to the opposite ends 150*a* and 150*b*. After forming the matrix 200, the threading devices 100 can be cut from the suture 150 and then the suture can be tied.

Figure 22:
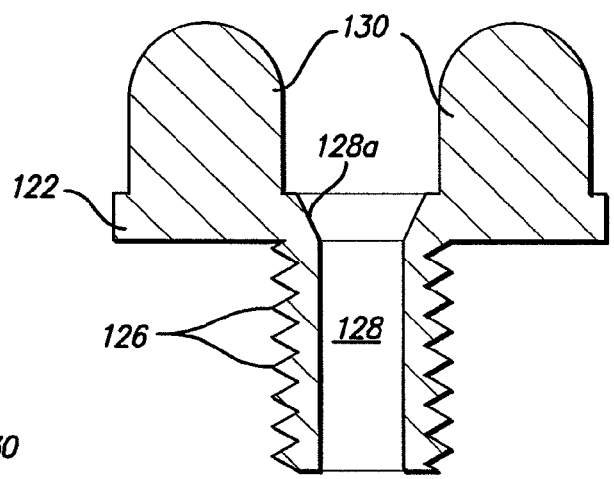
FIG. 22 is a sectional side elevational view of the threaded skin port of FIG. 21.
Figure 23:
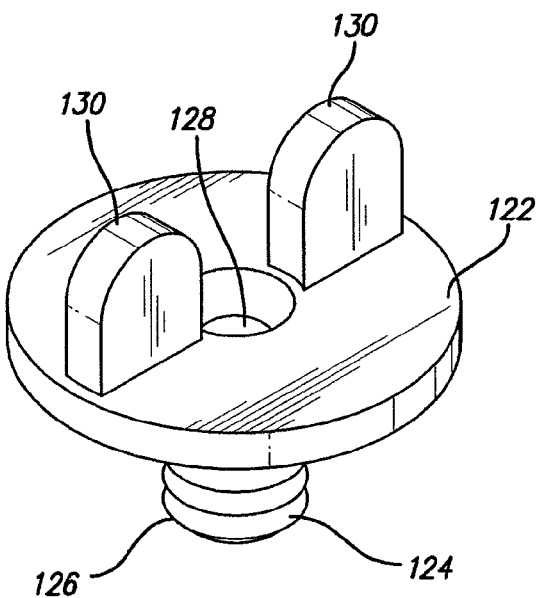
FIG. 23 is a perspective view of the threaded skin port of FIG. 21.

FIGS. 19-23 show the threaded skin port 120 used for the midline sub-mental access site. The threaded skin port 120 is inserted at the same time as the skin ports 80 described above. However, this is not a limitation on the present invention. The port 120 includes a flange 122 having a tube 124 extending therefrom. The tube 124 is preferably threaded 126. As is shown in FIG. 22, the tube 124 and flange 122 cooperate to define a tunnel 128 therethrough. In a preferred embodiment, the portion of the tunnel 128 in the flange 122 includes a beveled or tapered edge 128*a*.

In a preferred embodiment, the port 120 includes a pair of handle portions 130 extending upwardly from the flange 122 that aid the surgeon in threading the port 120 into the midline sub-mental access site. However, the handle portions 130 are not a limitation on the present invention and can be omitted. It will be understood that any skin port that allows access through the skin is within the scope of the present invention. For example, skin port 80 or something similar can be used at the midline sub-mental access site. In another embodiment, port 120 can be used at access site 14. In a preferred embodiment, port 120 is clear for aiding in the passage of the threading device 100. In other words, when the tip 104 of threading device 100 gets close to the port 120 it will transilluminate.

In use, the tube 124 is inserted into the midline sub-mental access site. The handle portions 130 are grasped and the port 120 is turned so that the threads 126 are threaded into the skin until the bottom surface of the flange 122 rests against the outer surface of the skin.

In another embodiment, a port similar to skin port 80 described above, but somewhat modified can be used for mid-line access. In this embodiment, the flange includes a threaded interior that engages the threads on the exterior of the tube. The distal ends of the folding members are connected to a ring that is not internally threaded. This ring allows the tube to rotate therein, but (because it is not internally threaded) does not cause the ring to ride up the threads of the tube. The opposite ends of the folding members are connected to the flange.

With this configuration, when the tube is rotated (preferably by engagement with the handset or with a surgeon's fingers), the threaded engagement of the exterior of the tube with the interior of the flange causes the tube to move outwardly (with respect to the interior of a patient's body). This action causes the folding members to fold at the crease. In use with a patient, in the folded position, the proximal end of the tube is located outside of the patient's body, and the distal end has moved closer to the flange than it was in the unfolded position.

Figure 18:
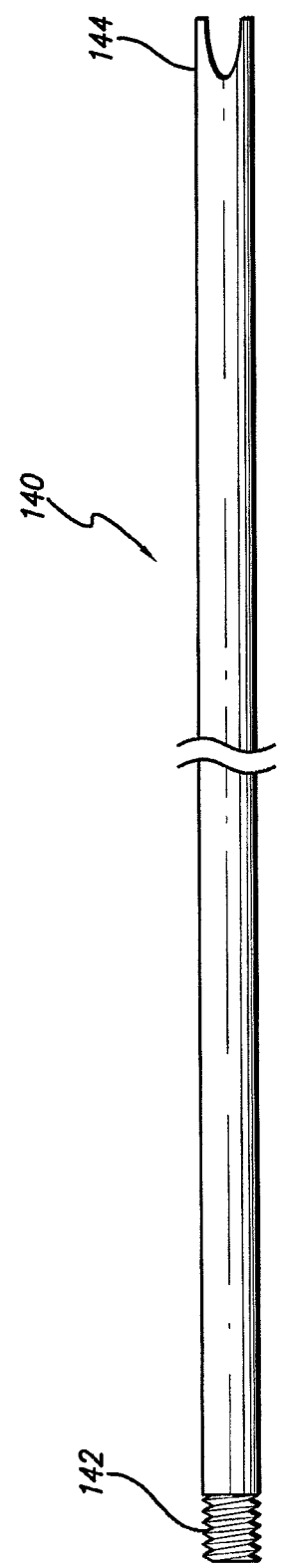
FIG. 18 is a side elevational view of a knot positioning implement in accordance with a preferred embodiment of the present invention.
Figure 19:
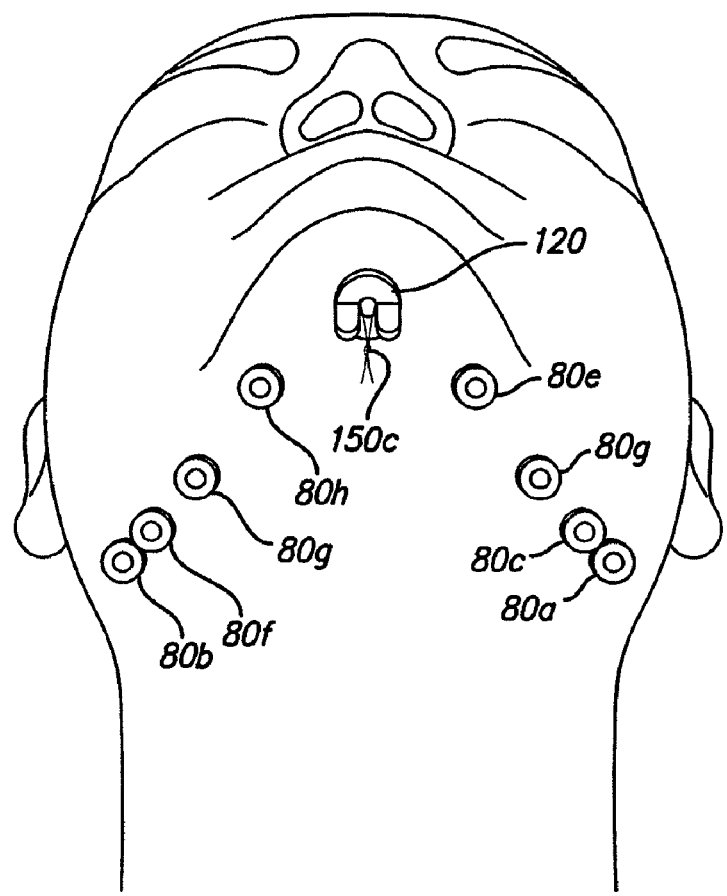
FIG. 19 is a view of a patient with a threaded skin port placed in the midline sub-mental access site and a suture knot extending therethrough.
Figure 20:
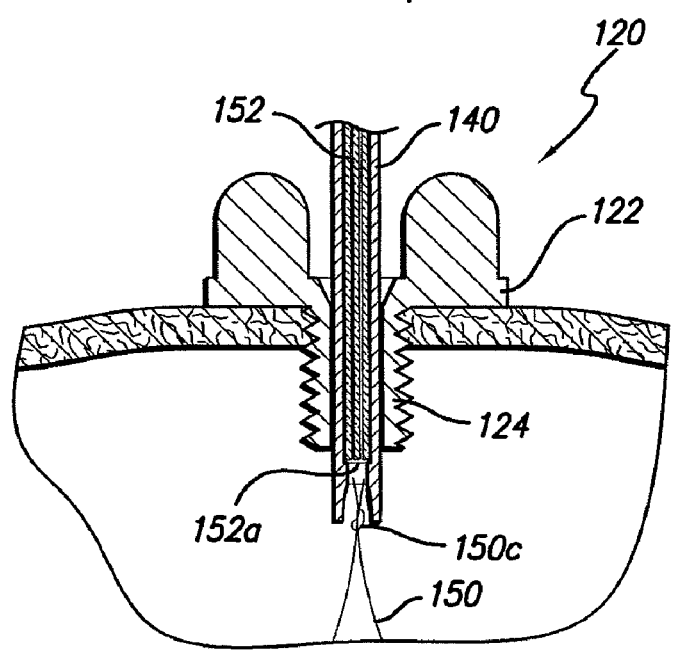
FIG. 20 is a cross-sectional view of the knot positioning implement of FIG. 15 pushing the knot through the threaded skin port and under a patient's skin.
Figure 21:
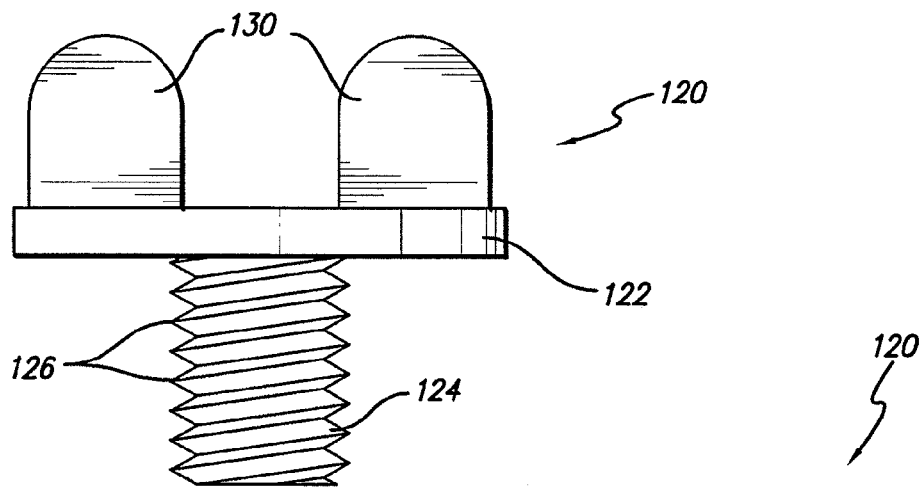
FIG. 21 is a side elevational view of a threaded skin port in accordance with a preferred embodiment of the present invention.

With reference to FIGS. 18-20, a knot positioning implement 140 is shown and described. After both ends 150*a* and 150*b* of the suture 150 are threaded and the support matrix 200 has been created, the two suture ends 150*a* and 150*b* are brought out through the midline sub-mental access site (through port 120), as is shown in FIG. 19. A single throw knot 150*c* is placed (it will be understood that the type of knot is not a limitation on the present invention) and the knot positioning implement 140 is utilized to set the knot 150*c*.

One end 142 of the knot positioning implement 140 (which is preferably threaded) docks with the handset 60 and the other end 144 is forked. The forked end 144 is used to push the knot 150*c* through the tunnel 128 of threaded skin port 120 and under the skin. In a preferred embodiment, the knot positioning implement 140 includes a fiber optic core 152 and an opening 152*a* through which light is transmitted to illuminate the work area when placing the knot 150*c*.

After the knot 150*c* has been pushed through the threaded port 120, threaded port 120 is twisted out of the access site and the other skin ports 80 are removed using the handset 60. To do this, the male connector 68 is inserted into the port 80 so that the ridge 68*a* snaps into the indented ring 82*a* and the teeth 68*b* and 82*b* engage one another. The handset 60 is then twisted, thereby turning tube 84 and causing the internally threaded ring 90*b* to travel back down threads 88 and unfolding folding the folding members 90*a*. In another embodiment, the ports 80 can be removed by hand.

After atraumatic removal of the ports 80 and 120, steristrips are then placed as desired and a neck compression garment is fitted onto the patient. See FIG. 25 for the final configuration of the exemplary support matrix 200.

Another exemplary embodiment of the construction of a support matrix 200 will now be described. Please see FIGS. 46-51. In this embodiment, handset 360 and threading device 300 are used. In this example, as shown in FIGS. 51-56 the majority of the access sites 14 are above the submandibular border. Because the threading device 300 is generally straight and needs to travel around the curvature of the jaw, it requires intermittent access sites 14 under the jaw to allow the threading rod to be redirected around the curvature of the neck (the exemplary access site showing this is marked 14*a*). The surgeon may choose to use other access sites under the patient's jaw or in other locations as needed to allow the threading rod to be redirected.

Figure 51:
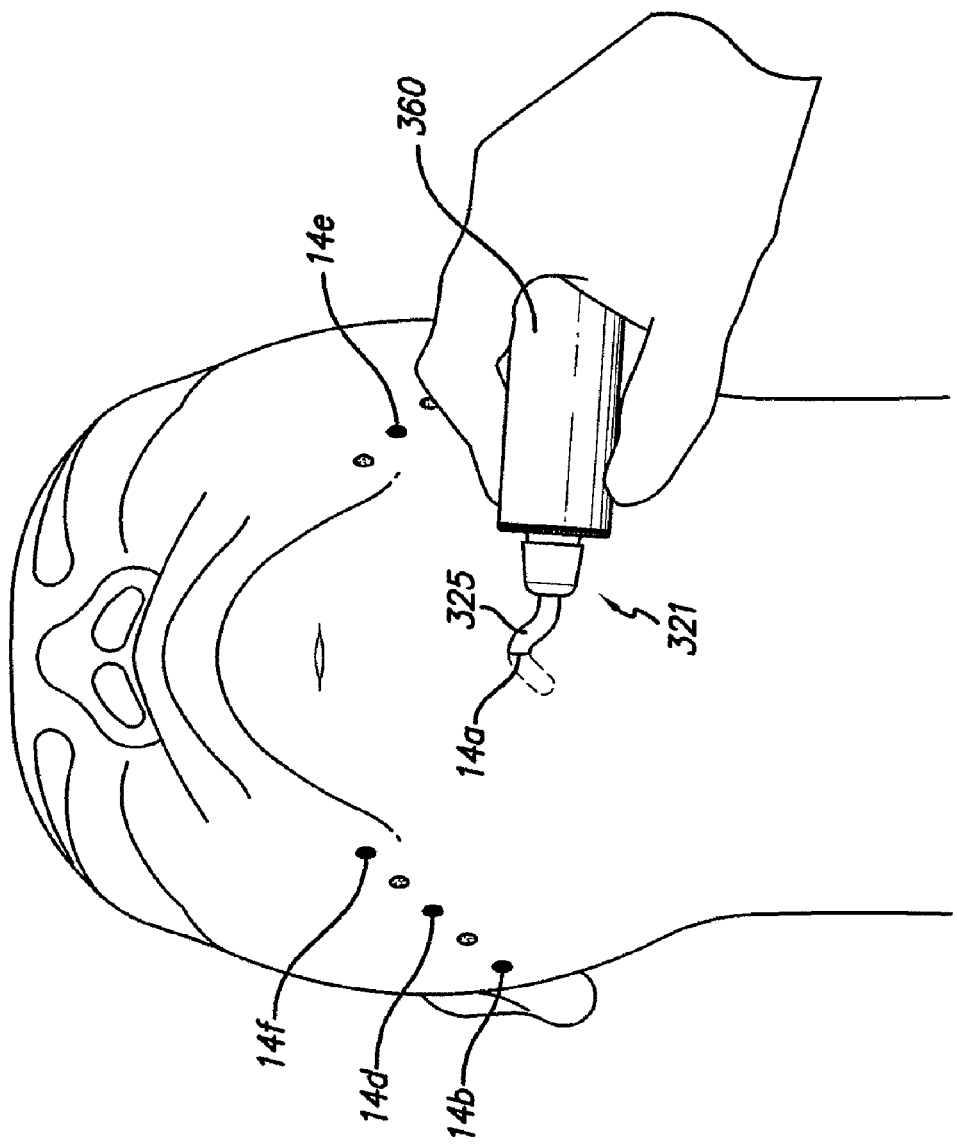
FIG. 51 is a view of a patient showing the use of a clearing device to clear an access site.

As shown in FIG. 51, before using the threading device, the surgeon may want to use clearing device 321 (or clearing device assembly 341) to clear dermal attachments under the area adjacent the access sites 14. Although not shown in the FIGS. 51-56, the surgeon can also use nose cone 339 or 339*b* to help secure the threading rod 300 and aid in the manipulation of the handset 360 during surgery.

For the initial entry of the threading device 300 and first suture 150 the surgeon creates an access site 14*a* under the chin. The handset 360 is illuminated (e.g., by pulling the rip cord, twisting or pushing the tail cone or otherwise switching the light source on) and the threading device 300 is inserted into the handset 360. Threading device 300 is inserted through access site 14*a*, as shown in FIG. 52. The lighted tip 304 of threading device 300 illuminates the work area and transilluminates through the skin allowing the surgeon to determine the proper placement of the support matrix 200 and the location of the tip 304.

The threading rod is then brought out through a second access site 14*b* and a portion of the suture is pulled through second access site 14*b*. Enough of the suture is pulled through second access site 14*b* so that just enough of the suture is still sticking out of site 14*a* so that the suture can be tied off at the end of the procedure (described below). To prevent the end of the suture from being pulled into first access site 14*a* it can be anchored by something, such as a hemostat. It will be understood that because the suture is tied in the middle of the threading rod 300, the surgeon does not have to pull the entire threading rod out of the access site. Instead, after over half of the threading rod is pulled through the site and the suture is pulled through, the surgeon can pivot the rod in the desired direction and then start pushing the rod back through the access site. This action allows the suture to anchor on the ligaments under the skin near the access site. It will be understood that because the threading rod 300 has the suture attached near the middle thereof and it is double ended, it does not have to be turned around each time it is brought out from under the patient's skin. However, the surgeon may turn the threading rod around as desired.

Before pushing the threading rod back into second access site 14b, the surgeon places the handset on the end of the threading rod to illuminate the tip 304, as shown in FIG. 53.

The threading rod is then threaded from site 14b to site 14a, is pivoted around and is passed subcutaneously to third access site 14c. Depending on the patient, the surgeon may thread straight from site 14b to site 14c without pivoting the rod at 14a. This is repeated for fourth, fifth and sixth access sites 14d, 14e and 14f and eventually the threading rod is brought out through the sub-mental access site (each time, the surgeon does not always have to come back out through site 14a but may go directly to the next site in the "shoe lace"). It will be understood that the handset is taken on and off of the threading rod as desired during this procedure so that one of the tips 304 is lit as desired. The suture 150 is then cut from the threading rod. Preferably, each time the threading device and suture 150 are passed through an access point 14, the first suture 150 is passed around the facial retaining ligaments adjacent thereto, thereby creating an anchor or pivot point.

Figure 54:
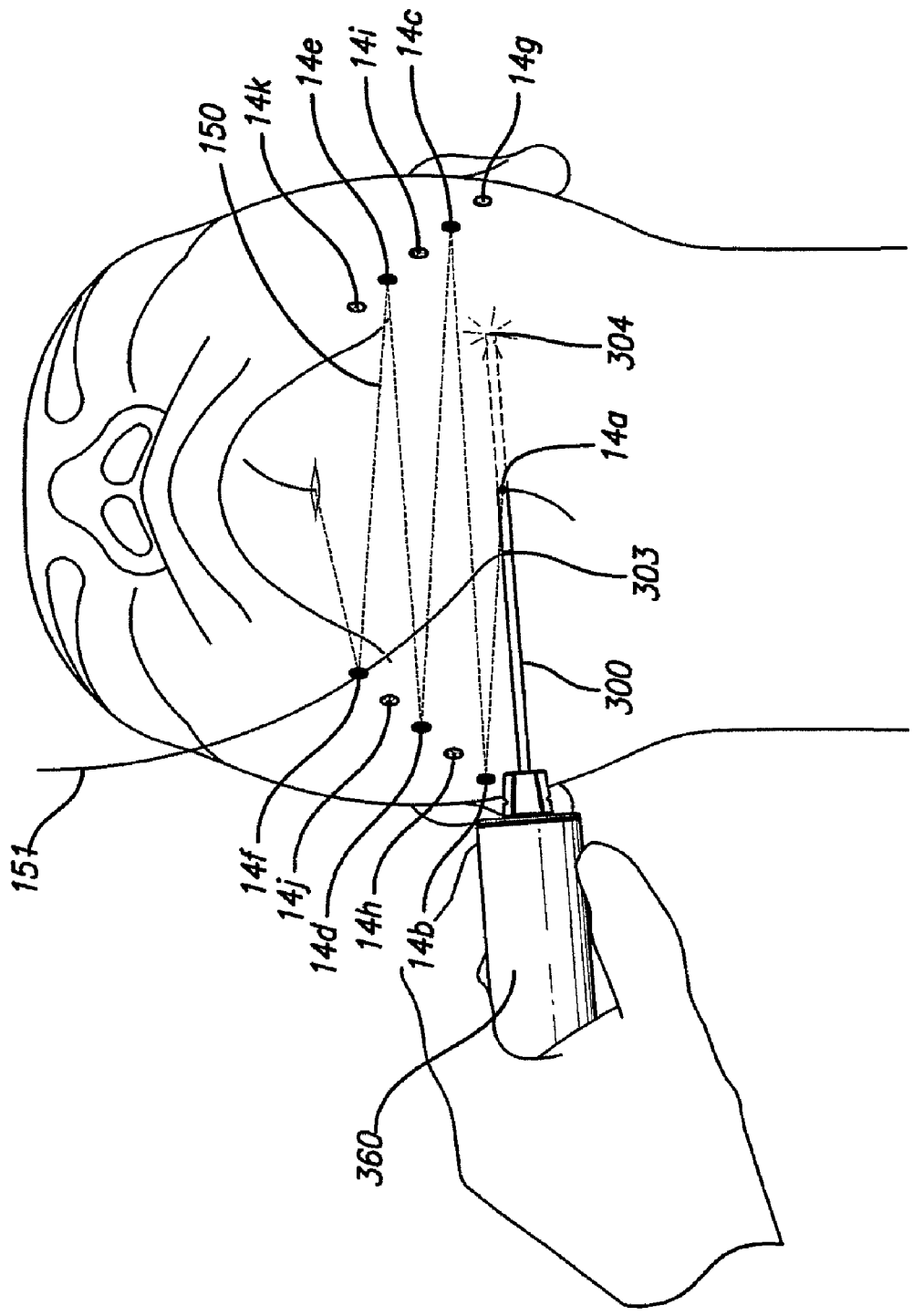
FIG. 54 is a view of a patient showing insertion of the threading rod and second suture into access site 14a using the handset after the entire first suture has been placed.
Figure 55:
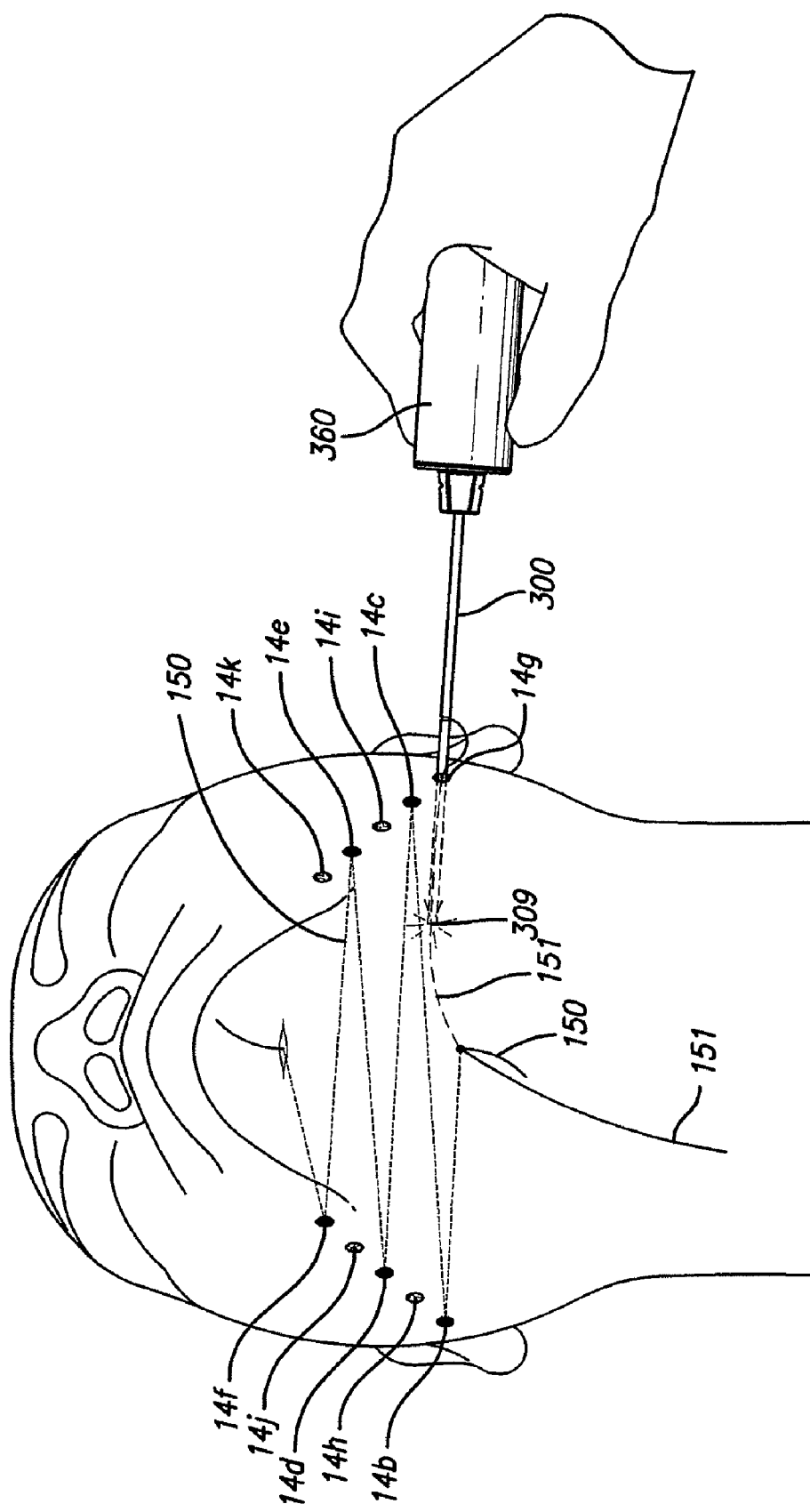
FIG. 55 is a view of a patient showing insertion of the threading rod and second suture into access site 14g after pivoting the threading rod.

As shown in FIG. 54, a second suture 151 is then tied to the threading rod 300 and the threading rod is inserted into first access site 14a. It is then passed subcutaneously to seventh access site 14g. Similar to the procedure described above for the first suture 150, the second suture 151 is then threaded to eighth, ninth, tenth and eleventh access sites 14h, 14i, 14j and 14k (see FIG. 55) and is finally brought out of the midline sub-mental access site. The ends of the sutures 150 and 151 extending out of site 14a are then tied together, thereby, completing the matrix 200 (see FIG. 56). The knot 150c is then pushed through the site 14a and under the skin (e.g., using the clearing device or threading rod). At this point, the surgeon can pull on the ends of the sutures 150 and 151 extending out of the sub-mental access site to place the desired tension on the matrix 200. Once this is done, the ends of the sutures 150 and 151 are tied together and the knot 150c is pushed through the site and under the skin.

It will be understood that the surgery can be performed without the handset. Some surgeons may want to use the threading device alone without using the handset to illuminate the tips. In this situation a solid threading device or a threading device with self-contained power and light sources can be used. It will be further understood that the threading device 300 can be used for other types of surgery. For example, it can be used to place suture systems that are commonly utilized in plastic surgery that previously required the opening or elevation of the facial, neck skin and/or other areas of the body. Examples of this include the use of this device or system for placement of a neck defining suture or it can be used in the MACS-lift (minimal access cranial suspension), which is described in The MACS-lift Short Scar Rhytidectomy by Patrick Tonnard, M.D. and Alexis Merpaile, M.D., Aesthetic Surgery Journal, Volume 27, Number 2, pgs. 188-198, March/April 2007, which is incorporated by reference in its entirety herein. In this procedure, "pursestring" sutures are used. To place the sutures, the surgeon could use the threading rod 300 instead of making the incisions that are typically made.

The neck defining suture, as it is known in the art, is described in the article Suture Suspension Platysmaplasty for Neck Rejuvenation Revisited: Technical Fine Points for Improving Outcomes by Vincent Giampapa, M.D., Ioannis Bitzos, M.D., Oscar Ramirez, M.D., and Mark Granick, M.D., Aesthetic Plastic Surgery, Vol. 29, pgs. 341-350, 2005, which is incorporated by reference in its entirety herein. However, instead of having to make large incisions and elevating the skin under the neck region, the procedure can be performed by making a small incision behind the ears and then threading the suture subcutaneously under the mandible using the threading rod 300 and necessary pivot points (access sites) as desired.

Figure 24:
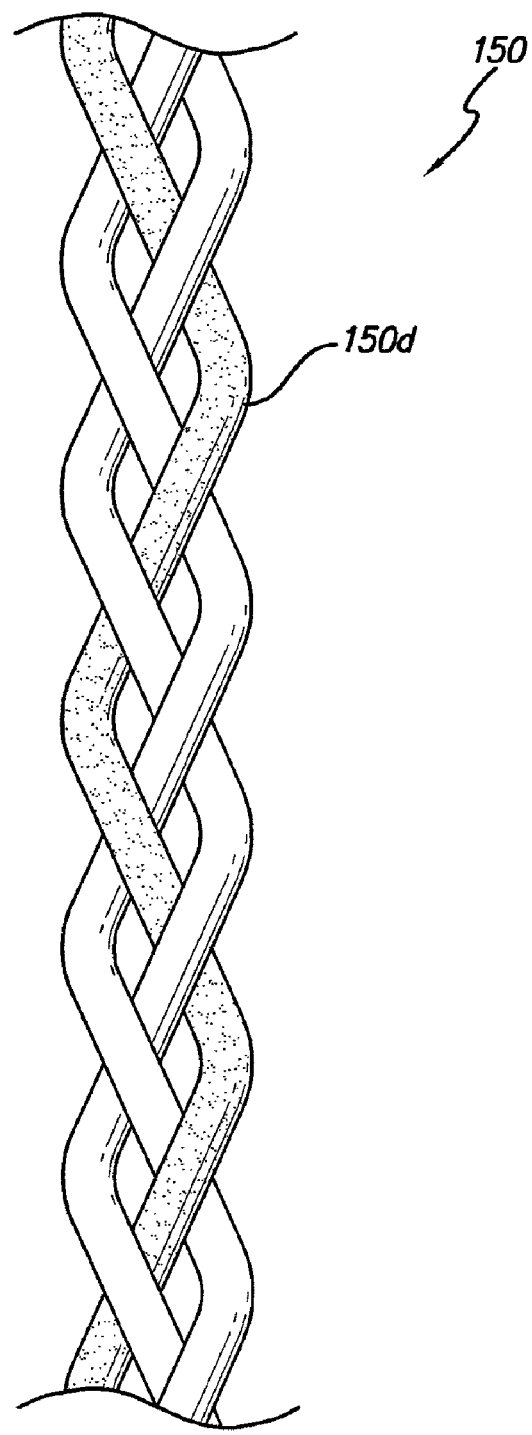
FIG. 24 is a side elevational view of a fiberoptic suture in accordance with a preferred embodiment of the present invention.

In a preferred embodiment, the suture that is used in the procedure is a 4.0 braided polyester suture. In a more preferred embodiment, as shown in FIG. 24, the suture design contains at least one fiberoptic strand 150d intertwined with the non-fiberoptic strands. The suture 150 is braided as is known in the art with one, two or three fiberoptic strands and one or two non-fiberoptic strands, as is desired. This aids in the transillumination of the suture 150 to check subcutaneous placement after the suture 150 has been placed. The fiberoptic strand 150d will illuminate when the handset 60 fiberoptic light coupled with the knot placement implement 140 is approximated to the suture during tying. Light transmitted to the suture allows the surgeon to visualize placement of the support matrix 200 as it is secured. The non-fiberoptic strands can be made of any material known in the art, such as nylon, polypropylene, or other non-absorbable material.

At any point during the creation of the support matrix 200, suture placement can be confirmed by placing the handset 60 or 360 (or any light source) at one of the ends 150a or 150b of the suture 150, thereby transmitting light down the fiberoptic strand 150d to check placement of the suture 150.

The illumination of the suture pathway allows the surgeon to determine the location of the suture. Overall, suture illumination gives the surgeon feedback relating to the anatomical movement of each pivot point.

It will be appreciated by those skilled in the art that the fiberoptic suture can be utilized in all areas of surgery or other materials where a lit binding material is needed, and not just in the technique described herein. In another embodiment, the threading device may be a straight or curved needle. Application of light energy during a surgical procedure will confirm suture placement and accuracy. Application of light postoperatively could allow surgeons to understand the evolution of suture placement related to time and aging.

In an alternative embodiment, the neck skin can be elevated from the platysma muscle via an incision similar to that used in the standard procedure discussed above to allow the surgeon to visualize the operative field and then the suture matrix can be placed through the ports 80 and/or access sites 14.

It is contemplated that the above described instruments can be sold in kits. For example, a kit with all or any combination of the instruments, including the tape 10 or 310, a marking pen, lancet 40, handset 60 or 360, skin ports 80, threading device 100 or 300, threaded skin port 120, knot positioning implement 140, suture 150 or 151, nose cone 339 or 339, clearing device 321, clearing device assembly 341 or any other instrument described herein can be sold.

The embodiments described above are exemplary embodiments of the present invention. Those skilled in the art may now make numerous uses of, and departures from, the above-described embodiments without departing from the inventive concepts disclosed herein. Accordingly, the present invention is to be defined solely by the scope of the following claims.

What is claimed is:

1. A method for threading a suture in a patient's body comprising the steps of:
   a) providing a suture,
   b) providing a threading device comprising an elongated rod having a suture tie-off location and first and second ends, c) tying the suture to the suture tie-off location,
d) inserting the first end of the elongated rod through a first opening in the patient's skin,
e) passing the first end of the elongated rod subcutaneously to a second opening in the patient's skin,
f) pulling the first end of the elongated rod and a portion of the suture through the second opening, and
g) without turning the elongated rod around, reinserting the first end of the threading device through the second opening in the skin and passing the second end of the elongated rod subcutaneously to a third opening in the patient's skin,
wherein at least one point during the performance of the method the first end of the elongated rod extends out of the second opening and the second end of the elongated rod extends out of the first opening.

2. The method of claim 1 wherein the suture tie-off location comprises a groove defined in the rod that extends substantially circumferentially around the rod.

3. The method of claim 1 wherein the suture tie-off location comprises an eyelet extending through the rod.

4. The method of claim 1 wherein the suture tie-off location is disposed at a location remote from the first and second ends.

5. The method of claim 1 wherein the suture tie-off location is disposed at a location that is approximately halfway between the first and second ends.

6. The method of claim 1 further comprising the step of illuminating the first end of the elongated rod before step (e).

7. The method of claim 1 wherein the first and second ends of the threading device are each lighted at predetermined points during the method.

8. The method of claim 6 wherein the first end of the rod is illuminated by a lighting device having an opening into which the second end of the rod is received.

9. The method of claim 7 wherein the first and second ends of the rod are illuminated at different points during performance of the method by a lighting device having an opening into which the first and second ends of the rod can be received.

10. A method of performing plastic surgery, the method comprising the steps of:
a. forming an opening in the patient's skin to form a mid-line access site,
b. forming at least first and second openings in the skin at a plurality of predetermined access sites,
c. providing a threading device having a suture secured thereto, and
d. inserting the threading device and suture through the first opening in the skin,
e. pulling at least a portion of the threading device through the second opening in the skin,
f. reinserting the threading device through the second opening in the skin, and
g. pulling the threading device through the mid-line access site, thereby forming a suture matrix under the skin.

11. The method of claim 10 wherein the threading device has first and second ends that are each lighted at predetermined points during the surgery.

12. The method of claim 10 wherein the suture is secured to the threading device at a point that is approximately midway between its ends.

13. The method of claim 10 further comprising the steps of placing a tape template onto a portion of a patient's skin and marking a plurality of access sites before step (b).

14. The method of claim 10 further comprising the step of performing liposuction through the mid-line access site.

15. The method of claim 10 wherein after the suture matrix is formed, the entire suture matrix is subcutaneous and not viewable outside the patient's body.

16. A method for threading a suture in a patient's body comprising the steps of:
a) providing a threading device comprising an elongated rod having first and second ends and having a suture secured thereto,
b) inserting the first end of the elongated rod through a first opening in the patient's skin,
c) passing the first end of the elongated rod subcutaneously to a second opening in the patient's skin,
d) pulling the first end of the elongated rod and a portion of the suture through the second opening, and
e) reinserting the first end of the threading device through the second opening in the skin and passing the second end of the elongated rod subcutaneously to an opening in the patient's skin.

* * * * *